(12) United States Patent
Linker et al.

(10) Patent No.: US 6,258,957 B1
(45) Date of Patent: *Jul. 10, 2001

(54) N-ARYL-1,2,4-TRIAZOLIN-5-ONES

(75) Inventors: Karl-Heinz Linker; Kurt Findeisen, both of Leverkusen; Wilhelm Haas, Pulheim; Andreas Lender, Wuppertal; Klaus-Helmut Müller, Düsseldorf; Otto Schallner, Monheim; Christoph Erdelen, Leichlingen; Andreas Turberg, Erkrath; Norbert Mencke, Leverkusen, all of (DE)

(73) Assignee: Bayer Aktiengesellschaft, Leverkusen (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/973,538

(22) PCT Filed: May 28, 1996

(86) PCT No.: PCT/EP96/02287

§ 371 Date: Dec. 2, 1997

§ 102(e) Date: Dec. 2, 1997

(87) PCT Pub. No.: WO96/41535

PCT Pub. Date: Dec. 27, 1996

(30) Foreign Application Priority Data

Jun. 9, 1995 (DE) .............................................. 195 21 162

(51) Int. Cl.$^7$ .................................................. C07D 249/12
(52) U.S. Cl. .................................... 548/263.4; 548/263.8; 548/264.4
(58) Field of Search .................. 514/284; 548/263.4, 548/263.8, 264.4

(56) References Cited

U.S. PATENT DOCUMENTS

| | | |
|---|---|---|
| 4,818,275 | 4/1989 | Theodoridis . |
| 5,041,155 | 8/1991 | Theodoridis . |
| 5,174,809 | 12/1992 | Theodoridis . |
| 5,214,154 | 5/1993 | Theodoridis . |
| 5,256,793 | 10/1993 | Bailey, et al. . |
| 5,262,390 * | 11/1993 | Theodoridis ........................ 504/273 |
| 5,281,614 * | 1/1994 | Ashton et al. ....................... 514/359 |
| 5,294,595 | 3/1994 | Theodoridis . |
| 5,378,681 * | 1/1995 | Schallner et al. ................... 504/273 |
| 5,440,045 | 8/1995 | Bailey et al. . |
| 5,476,946 * | 12/1995 | Linker et al. ....................... 504/273 |

FOREIGN PATENT DOCUMENTS

| | | |
|---|---|---|
| 597360 * | 5/1994 | (EP) . |
| 617026 * | 9/1994 | (EP) . |
| 213 913 | 4/1993 | (HU) . |

OTHER PUBLICATIONS

Chang et al., "Potent triazolinone–based, etc" CA 122:150864 (1995).*
Theodoridis et al., "Synthesis and herbicidal, etc." CA 118:54226 (1993).*
Inaba et al., "Preparation of 1–phenyl–or 1–(2–pyridyl), etc." CA 113:97612 (1990).*
Coburn et al., "Picryl derivatives of 5–nitro, etc" CA 113: 78277 (1990).*
Evers et al., "Sructure and reactions of activated, etc" CA94:12143 (1981).*
Neuloeffer et al., "α–hydrozonocarboxylic acid azides, etc" CA 71:21770 (1969).*
Cram and Hammond, "Organic Chemistry", McGraw Hill Book Co., NY (1964) 2nd ed. pp 565–567.*

* cited by examiner

Primary Examiner—Patricia L. Morris
(74) Attorney, Agent, or Firm—Norris McLaughlin & Marcus

(57) ABSTRACT

The present invention relates to the use of partly known N-aryl-1,2,4-triazolin-5-ones of the formula (I)

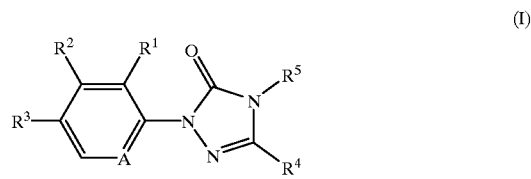

(I)

in which

A, $R^1$, $R^2$, $R^3$, $R^4$ and $R^5$ are each as defined in the description for controlling animal pests.

2 Claims, No Drawings

N-ARYL-1,2,4-TRIAZOLIN-5-ONES

The present invention relates to the use of novel and known N-aryl-1,2,4-triazolin-5-ones for controlling animal pests, in particular insects, arachnids and nematodes, encountered in agriculture, in forests, in the protection of store products and materials, and in the hygiene field.

It is already known that certain substituted N-aryl-1,2,4-triazolin-5-one derivatives have herbicidal properties (cf. for example EP-A-0 610 733 and EP-A-0 617 026). Nothing is known about an insecticidal activity of the compounds known from EP-A-0 617 026. The compounds known from EP-A-0 610 733 are claimed to have activity against leaf insects and acarids at the appropriate application rates. However, the insecticidal activity of these compounds, in particular at low application rates and concentrations, is not always satisfactory.

This invention, accordingly, provides novel and known N-aryl-1,2,4-triazolin-5-ones of the formula (I)

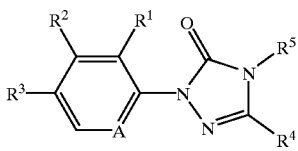

in which

A represents nitrogen or the group CR,

R represents hydrogen, halogen, nitro, cyano, hydroxyl, optionally halogen-, cyano-, nitro-, alkoxy- or amino-substituted alkyl, optionally substituted cycloalkyl or the radical —CX—NY$^1$Y$^2$, R$^1$ represents halogen, nitro, cyano, respectively optionally halogen-, cyano-, nitro-, alkoxy- or amino-substituted alkyl or alkoxy, optionally substituted cycloalkyl or the radical —CX—NY$^1$Y$^2$, R$^2$ represents hydrogen, halogen, optionally halogen-, cyano-, nitro-, alkoxy- or amino-substituted alkyl or optionally substituted cycloalkyl, R$^3$ represents nitro, halogenoalkyl, halogenoalkoxy or the radical —S(O)$_n$R$^6$, R$^4$ represents halogen, nitro, cyano, respectively optionally halogen-, cyano-, nitro-, alkoxy- or amino-substituted alkyl or alkoxy, represents alkenyl, alkenyloxy, alkinyl, hydroxyl, mercapto, respectively optionally substituted cycloalkyl or cycloalkylalkyl, respectively optionally substituted aryl, aryloxyalkyl or aralkyl or the radical —S(O)$_n$R$^6$, R$^5$ represents hydrogen, cyano, respectively optionally halogen-, cyano-, nitro-, alkoxy- or amino-substituted alkyl or alkoxy, represents alkenyl, alkenyloxy, alkinyl, alkinyloxy, respectively optionally substituted cycloalkyl or cycloalkylalkyl, respectively optionally substituted aryl or aralkyl or one of the radicals —S(O)$_n$R$^6$, —NR$^7$R$^8$ or —N=CR$^9$R$^{10}$, R$^6$ represents optionally halogen-, cyano-, nitro-, alkoxy- or amino-substituted alkyl, represents alkenyl, alkanedienyl, alkinyl, optionally substituted cycloalkyl or optionally substituted aryl, R$^7$ represents hydrogen, optionally halogen-, cyano-, nitro-, alkoxy- or amino-substituted alkyl, represents alkenyl, alkinyl, alkoxy, optionally substituted cycloalkyl or optionally substituted aryl, R$^8$ represents hydrogen, optionally halogen-, cyano-, nitro-, alkoxy- or amino-substituted alkyl, represents alkenyl, alkinyl, alkoxy, optionally substituted cycloalkyl or optionally substituted aryl, or R$^7$ and R$^8$ join with the linking nitrogen atom to represent an optionally substituted heterocycle which may optionally contain one or more additional hetero atoms, R$^9$ represents hydrogen, optionally halogen-, cyano-, nitro-, alkoxy- or amino-substituted alkyl, represents alkoxy, optionally substituted cycloalkyl or respectively optionally substituted aryl or heterocyclyl, R$^{10}$ represents hydrogen, optionally halogen-, cyano-, nitro-, alkoxy- or amino-substituted alkyl, represents alkoxy, optionally substituted cycloalkyl or respectively optionally substituted aryl or heterocyclyl, X represents oxygen or sulphur, Y$^1$ represents hydrogen or alkyl, Y$^2$ represents hydrogen or alkyl, and n represents one of the numbers 0, 1 or 2, which are highly suitable for controlling animal pests, in particular insects, arachnids and nematodes.

Depending on the nature of the substituents, the compounds of the formula (I) can be present as geometric and/or optical isomers or isomer mixtures of differing composition. The invention relates both to the pure isomers and to the isomer mixtures.

Surprisingly, the N-aryl-1,2,4-triazolin-5-ones used according to the invention have appreciably better activity against animal pests than the constitutionally most similar prior-art compounds.

Formula (I) provides a general definition of the N-aryl-1,2,4-triazolin-5-ones usable according to the invention.

Preferred substituents and ranges of the radicals recited in the formulae mentioned hereinabove and hereinbelow are illustrated in what follows.

A preferably represents nitrogen or the group CR.

R preferably represents hydrogen, fluorine, chlorine, bromine, nitro, cyano, hydroxyl, optionally fluorine-, chlorine-, cyano-, nitro- or $C_1$–$C_2$-alkoxy-substituted $C_1$–$C_4$-alkyl, optionally fluorine-, chlorine-, bromine-, $C_1$–$C_4$-alkyl-, $C_1$–$C_4$-alkoxy-, $C_1$–$C_4$-halogenoalkyl- or $C_1$–$C_4$-halogenoalkoxy-substituted $C_3$–$C_6$-cycloalkyl, or represents one of the radicals —CONH$_2$, —CSNH$_2$, —CO—NH—$C_1$–$C_4$-alkyl, —CS—NH—$C_1$–$C_4$-alkyl, —CO—N($C_1$–$C_4$-alkyl)$_2$, or —CS—N($C_1$–$C_4$-alkyl)$_2$.

R$^1$ preferably represents fluorine, chlorine, bromine, nitro, cyano, respectively optionally fluorine-, chlorine-, cyano-, nitro- or $C_1$–$C_2$-alkoxy-substituted $C_1$–$C_4$-alkyl or $C_1$–$C_4$-alkoxy, optionally fluorine-, chlorine-, bromine-, $C_1$–$C_4$-alkyl-, $C_1$–$C_4$-alkoxy-, $C_1$–$C_4$-halogenoalkyl- or $C_1$–$C_4$-halogenoalkoxy-substituted $C_3$–$C_6$-cycloalkyl, or represents one of the radicals —CONH$_2$, —CSNH$_2$, —CO—NH—$C_1$–$C_4$-alkyl, —CS—NH—$C_1$–$C_4$-alkyl, —CO—N($C_1$–$C_4$-alkyl)$_2$, or —CS—N($C_1$–$C_4$-alkyl)$_2$.

R$^2$ preferably represents hydrogen, fluorine, chlorine, $C_1$–$C_4$-alkyl or $C_1$–$C_4$-halogenoalkyl.

R$^3$ preferably represents nitro, $C_1$–$C_4$-halogenoalkyl, $C_1$–$C_4$-halogenoalkoxy or one of the radicals —S—$C_1$–$C_4$-halogenoalkyl, —SO—$C_1$–$C_4$-halogenoalkyl, or —SO$_2$—$C_1$–$C_4$-halogenoalkyl.

R$^4$ preferably represents halogen, nitro, cyano, respectively optionally fluorine-, chlorine-, cyano-, nitro-, $C_1$–$C_4$-alkoxy- or amino-substituted $C_1$–$C_4$-alkyl or $C_1$–$C_4$-alkoxy, represents $C_3$–$C_6$-alkenyl, $C_3$–$C_6$-alkenyloxy, $C_3$–$C_6$-alkinyl, hydroxyl, mercapto, respectively optionally fluorine-, chlorine-, bromine-, $C_1$–$C_4$-alkyl-, $C_1$–$C_4$-alkoxy-, $C_1$–$C_4$-halogenoalkyl- or $C_1$–$C_4$-halogenoalkoxy-substituted $C_3$–$C_6$-cycloalkyl or $C_3$–$C_6$-cycloalkyl-$C_1$–$C_4$-alkyl, represents phenyl, phenyloxy-$C_1$–$C_4$-alkyl or phenyl-$C_1$–$C_4$-alkyl, each of which is optionally substituted by halogen, cyano, nitro, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy, $C_1$–$C_4$-halogenoalkylthio or optionally halogen- or $C_1$–$C_4$-alkyl-substituted phenyl, or represents the radical —S(O)$_n$R$^6$.

$R^5$ preferably represents hydrogen, cyano, respectively optionally fluorine-, chlorine-, cyano-, nitro-, $C_1$–$C_4$-alkoxy- or amino-substituted $C_1$–$C_4$-alkyl or $C_1$–$C_4$-alkoxy, represents $C_3$–$C_6$-alkenyl, $C_3$–$C_6$-alkenyloxy, $C_3$–$C_6$-alkinyl, $C_3$–$C_6$-alkinyloxy, respectively optionally fluorine-, chlorine-, bromine-, $C_1$–$C_4$-alkyl-, $C_1$–$C_4$-alkoxy-, $C_1$–$C_4$-halogenoalkyl- or $C_1$–$C_4$-halogenoalkoxy-substituted $C_3$–$C_6$-cycloalkyl, or $C_3$–$C_6$-cycloalkyl-$C_1$–$C_4$-alkyl, phenyl which is optionally substituted by halogen, cyano, nitro, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy, $C_1$–$C_4$-halogenoalkylthio or optionally halogen- or $C_1$–$C_4$-alkyl-substituted phenyl, represents $C_1$–$C_4$-alkyl-substituted benzyl or one of the radicals —S(O)$_n$R$^6$, —NR$^7$R$^8$ or —N=CR$^9$R$^{10}$.

$R^6$ preferably represents optionally fluorine-, chlorine-, cyano- or nitro-substituted $C_1$–$C_4$-alkyl, represents $C_3$–$C_6$-alkenyl, $C_3$–$C_6$-alkanedienyl, $C_3$–$C_6$-alkinyl, optionally fluorine-, chlorine-, bromine-, $C_1$–$C_4$-alkyl-, $C_1$–$C_4$-alkoxy-, $C_1$–$C_4$-halogenoalkyl- or $C_1$–$C_4$-halogenoalkoxy-substituted $C_3$–$C_6$-cycloalkyl, or phenyl which is optionally substituted by halogen, cyano, nitro, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy, $C_1$–$C_4$-halogenoalkylthio or optionally halogen- or $C_1$–$C_4$-alkyl-substituted phenyl.

n preferably represents one of the numbers 0, 1 or 2.

$R^7$ preferably represents hydrogen, optionally fluorine-, chlorine-, cyano-, nitro-, amino- or $C_1$–$C_4$-alkoxy-substituted $C_1$–$C_4$-alkyl, represents $C_3$–$C_6$-alkenyl, $C_3$–$C_6$-alkinyl or $C_1$–$C_4$-alkoxy, optionally fluorine-, chlorine-, bromine-, $C_1$–$C_4$-alkyl-, $C_1$–$C_4$-alkoxy-, $C_1$–$C_4$-halogenoalkyl- or $C_1$–$C_4$-halogenoalkoxy-substituted $C_3$–$C_6$-cycloalkyl, or phenyl which is optionally substituted by halogen, cyano, nitro, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy, $C_1$–$C_4$-halogenoalkylthio or optionally halogen- or $C_1$–$C_4$-alkyl-substituted phenyl.

$R^8$ preferably represents hydrogen, optionally fluorine-, chlorine-, cyano-, nitro-, amino- or $C_1$–$C_4$-alkoxy-substituted $C_1$–$C_4$-alkyl, represents $C_3$–$C_6$-alkenyl, $C_3$–$C_6$-alkinyl or $C_1$–$C_4$-alkoxy, optionally fluorine-, chlorine-, bromine-, $C_1$–$C_4$-alkyl-, $C_1$–$C_4$-alkoxy-, $C_1$–$C_4$-halogenoalkyl- or $C_1$–$C_4$-halogenoalkoxy-substituted $C_3$–$C_6$-cycloalkyl, or phenyl which is optionally substituted by halogen, cyano, nitro, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy, $C_1$–$C_4$-halogenoalkylthio or optionally halogen- or $C_1$–$C_4$-alkyl-substituted phenyl, or $R^7$ and $R^8$ to preferably join with the linking nitrogen atom to represent an optionally halogen-, $C_1$–$C_4$-alkyl-, $C_1$–$C_4$-alkoxy- or $C_1$–$C_4$-alkylthio-substituted saturated 5- to 7-membered heterocycle having, in addition to the nitrogen atom, 2 or 3 identical or different hetero atoms from the group consisting of nitrogen, oxygen and sulphur.

$R^9$ preferably represents hydrogen, optionally fluorine-, chlorine-, cyano-, nitro-, amino- or $C_1$–$C_4$-alkoxy-substituted $C_1$–$C_4$-alkyl or represents $C_1$–$C_4$-alkoxy.

$R^{10}$ preferably represents hydrogen, optionally fluorine-, chlorine-, cyano-, nitro-, amino- or $C_1$–$C_4$-alkoxy-substituted $C_1$–$C_4$-alkyl or represents $C_1$–$C_4$-alkoxy.

A particularly preferably represents nitrogen or the group CR.

R particularly preferably represents hydrogen, fluorine, chlorine, bromine, nitro, cyano, hydroxyl, methyl, ethyl, n- or i-propyl, methoxymethyl, trifluoromethyl, difluoromethyl, chlorodifluoromethyl, dichlorofluoromethyl or represents one of the radicals —CONH$_2$, —CSNH$_2$, —CONHCH$_3$, —CSNHCH$_3$, —CON(CH$_3$)$_2$ or —CSN(CH$_3$)$_2$.

$R^1$ particularly preferably represents fluorine, chlorine, bromine, nitro, cyano, methyl, ethyl, n- or i-propyl, methoxymethyl, trifluoromethyl, difluoromethyl, chlorodifluoromethyl, dichlorofluoromethyl, trifluoromethoxy, difluoromethoxy, trifluoroethoxy or one of the radicals —CONH$_2$, —CSNH$_2$, —CONHCH$_3$, —CSNHCH$_3$, —CON(CH$_3$)$_2$ and —CSN(CH$_3$)$_2$.

$R^2$ particularly preferably represents hydrogen, fluorine, chlorine, methyl or trifluoromethyl.

$R^3$ particularly preferably represents trifluoromethyl, difluoromethyl, chlorodifluoromethyl, dichlorofluoromethyl, trifluoromethoxy, difluoromethoxy, chlorodifluoromethoxy, trifluoromethylsulphenyl, trifluoromethylsulphinyl or trifluoromethylsulphonyl.

$R^4$ particularly preferably represents chlorine, bromine, nitro, cyano, methyl, ethyl, n- or i-propyl, n-, i-, s- or t-butyl, methoxy, ethoxy, n- or i-propoxy, n-, i-, s- or t-butoxy, methoxymethyl, methoxyethyl, ethoxymethyl, ethoxyethyl, trifluoromethyl, difluoromethyl, chlorodifluoromethyl, dichlorofluoromethyl, trifluoroethyl, tetrafluoroethyl, pentafluoroethyl, fluoropropyl, trifluoromethoxy, difluoromethoxy, chlorodifluoromethoxy, dichlorofluoromethoxy, trifluoroethoxy, tetrafluoroethoxy, pentafluoroethoxy, cyanomethyl, allyl, allyloxy, propargyl, hydroxyl, mercapto, respectively optionally fluorine-, chlorine-, bromine-, methyl-, ethyl-, methoxy-, trifluoromethyl- or trifluoromethoxy-substituted cyclopropyl, cyclopropylmethyl, cyclopentyl, cyclopentylmethyl, cyclohexyl or cyclohexylmethyl, represents phenyl, phenoxymethyl or benzyl, each of which is optionally substituted by fluorine, chlorine, methyl, methoxy, trifluoromethyl, trifluoromethoxy, methylthio, trifluoromethylthio, nitro, or optionally fluorine-, chlorine- or methyl-substituted phenyl, or represents the radical —S(O)$_n$R$^6$.

$R^5$ particularly preferably represents hydrogen, cyano, methyl, ethyl, n- or i-propyl, n-, i-, s- or t-butyl, methoxy, ethoxy, n- or i-propoxy, n-, i-, s- or t-butoxy, methoxymethyl, methoxyethyl, ethoxymethyl, ethoxyethyl, difluoromethyl, chlorodifluoromethyl, dichlorofluoromethyl, trifluoroethyl, fluoropropyl, difluoromethoxy, chlorodifluoromethoxy, dichlorofluoromethoxy, cyanomethyl, allyl, allyloxy, propargyl, propargyloxy, butinyloxy, respectively optionally fluorine-, chlorine-, bromine-, methyl-, ethyl-, methoxy-, trifluoromethyl- or trifluoromethoxy-substituted cyclopropyl, cyclopropylmethyl, cyclopentyl, cyclopentylmethyl, cyclohexyl or cyclohexylmethyl, represents phenyl which is optionally substituted by fluorine, chlorine, methyl, methoxy, trifluoromethyl, trifluoromethoxy, methylthio, trifluoromethylthio, cyano, nitro, or optionally fluorine-, chlorine- or methyl-substituted phenyl, represents optionally methyl-, ethyl-, n- or i-propyl-, n-, i-, s- or t-butyl-substituted benzyl or represents one of the radicals —S(O)$_n$R$^6$, —NR$^7$R$^8$ or —N=CR$^9$R$^{10}$.

$R^6$ particularly preferably represents methyl, ethyl, n- or i-propyl, n-, i-, s- or t-butyl, trifluoromethyl, difluoromethyl, chlorodifluoromethyl, dichlorofluoromethyl, trifluoroethyl, tetrafluoroethyl, pentafluoroethyl, fluoropropyl, allyl, allenyl, propargyl, respectively optionally fluorine-, chlorine-, bromine-, methyl-, ethyl-, methoxy-, trifluoromethyl- or trifluoromethoxy-substituted cyclopropyl, cyclopentyl or cyclohexyl, or phenyl which is optionally substituted by fluorine, chlorine, methyl, methoxy, trifluoromethyl, trifluoromethoxy, methylthio, trifluoromethylthio, cyano, nitro, or optionally fluorine-, chlorine- or methyl-substituted phenyl.

n particularly preferably represents one of the numbers 0, 1 or 2.

$R^7$ particularly preferably represents hydrogen, methyl, ethyl, n- or i-propyl, n-, i-, s- or t-butyl, methoxy, ethoxy or cyclopropyl.

$R^8$ particularly preferably represents hydrogen, methyl, ethyl, n- or i-propyl, n-, i-, s- or t-butyl, methoxy, ethoxy or cyclopropyl, or $R^7$ and $R^8$ particularly preferably join with the linking nitrogen atom to represent respectively optionally methyl-, ethyl-, methoxy- or ethoxy-substituted piperidinyl, piperazinyl or morpholinyl.

$R^9$ particularly preferably represents hydrogen, methyl, ethyl, n- or i-propyl, n-, i-, s- or t-butyl, -methoxy or ethoxy.

$R^{10}$ particularly preferably represents hydrogen, methyl, ethyl, n- or i-propyl, n-, i-, s- or t-butyl, methoxy or ethoxy.

Some of the compounds of the formula (I) are known (see for example EP-A 0 617 026).

The abovementioned radical definitions or illustrations mentioned generally or in preferred ranges apply to the end products and, correspondingly, to the starting materials and intermediates. These radical definitions can be combined with each other as desired, i.e. also between the respective preferred ranges.

According to the invention, preference is given to using compounds of the formula (I) in which there exists a combination of the meanings mentioned above as preferred.

According to the invention, particular preference is given to using compounds of the formula (I) in which there exists a combination of the meanings mentioned above as particularly preferred.

Hydrocarbon radicals such as alkyl or alkenyl mentioned in the radical definitions hereinabove and hereinbelow can, as far as possible, in each case be straight-chain or branched, including in conjunctions with hetero atoms, e.g. alkoxy or alylthio.

The novel N-aryl-1,2,4-triazolin-5-ones usable according to the invention have the formula (Ia)

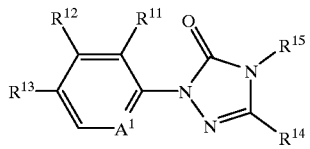

in which $A^1$ represents nitrogen or the group $CR^o$, $R^o$ represents hydrogen, halogen, nitro, cyano, hydroxyl, optionally halogen-, cyano-, nitro-, alkoxy- or amino-substituted alkyl, optionally substituted cycloalkyl or the radical —CX$^1$—NY$^{11}$Y$^{12}$, $R^{11}$ represents halogen, nitro, cyano, respectively optionally halogen-, cyano-, nitro-, alkoxy- or amino-substituted alkyl or alkoxy, optionally substituted cycloalkyl or the radical —CX$^1$—NY$^{11}$Y$^{12}$, $R^{12}$ represents hydrogen, halogen, optionally halogen-, cyano-, nitro-, alkoxy- or amino-substituted alkyl or optionally substituted cycloalkyl, $R^{13}$ represents nitro, halogenoalkyl, halogenoalkoxy or the radical —S(O)$_n$$^1$R$^{16}$, $R^{14}$ represents halogen, cyano, respectively optionally halogen-, cyano-, nitro-, alkoxy- or amino-substituted alkyl or alkoxy, represents alkenyl, alkenyloxy, alkinyl, hydroxyl, mercapto, respectively optionally substituted cycloalkyl or cycloalkylalkyl, respectively optionally substituted aryl, aryloxyalkyl or aralkyl or the radical —S(O)$_n$$^1$R$^{16}$, $R^{15}$ represents hydrogen, cyano, amino, respectively optionally halogen-, cyano-, nitro-, alkoxy- or amino-substituted alkyl or alkoxy, represents alkenyl, alkenyloxy, alkinyl, alkinyloxy, respectively optionally substituted cycloalkyl or cycloalkylalkyl, respectively optionally substituted aryl or aralkyl or one of the radicals —S(O)$_n$$^1$R$^{16}$, NR$^{17}$R$^{18}$ or —N=CR$^{19}$R$^{20}$, $R^{16}$ represents optionally halogen-, cyano-, nitro-, alkoxy- or amino-substituted alkyl, represents alkenyl, alkanedienyl, alkinyl, optionally substituted cycloalkyl or optionally substituted aryl, $R^{17}$ and $R^{18}$ join with the linking nitrogen atom to represent an optionally substituted heterocycle which may optionally contain one or more additional hetero atoms, $R^{19}$ represents hydrogen, optionally halogen-, cyano-, nitro-, alkoxy- or amino-substituted alkyl, represents alkoxy, optionally substituted cycloalkyl or respectively optionally substituted aryl or heterocyclyl, $R^{20}$ represents hydrogen, optionally halogen-, cyano-, nitro-, alkoxy- or amino-substituted alkyl, represents alkoxy, optionally substituted cycloalkyl or respectively optionally substituted aryl or heterocyclyl, $X^1$ represents oxygen or sulphur, $Y^{11}$ represents hydrogen or alkyl, $Y^{12}$ represents hydrogen or alkyl, and n represents one of the numbers 0, 1 or 2.

Depending on the nature of the substituents, the compounds of the formula (Ia) can be present as geometric and/or optical isomers or isomer mixtures of differing composition. The invention relates both to the pure isomers and to the isomer mixtures.

Furthermore, it was found that
a) N-aryl-1,2,4-triazolin-5-ones of the formula (Ia)

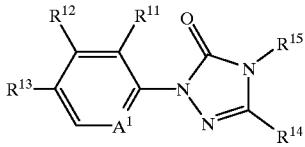
(Ia)

in which

R$^{11}$, R$^{12}$, R$^{13}$, R$^{14}$, R$^{15}$ and A$^{1}$ are each as defined above are obtained when 1H-triazolinones of the formula (II)

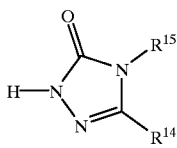
(II)

in which

R$^{14}$ and R$^{15}$ are each as defined above are reacted with halogen derivatives of the formula (III)

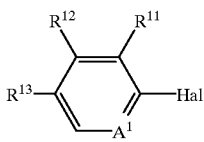
(III)

in which

R$^{11}$, R$^{12}$, R$^{13}$ and A$^{1}$ are each as defined above and

Hal represents halogen, if appropriate in the presence of a diluent and if appropriate in the presence of a reaction auxiliary; or b) N-aryl-1,2,4-triazolin-5-ones of the formula (Ib)

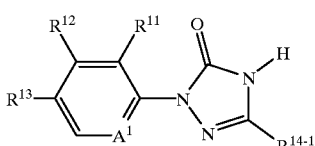
(Ib)

in which

R$^{11}$, R$^{12}$, R$^{13}$, and A$^{1}$ are each as defined above and

R$^{14-1}$ represents cyano, respectively optionally halogen-, cyano-, nitro-, alkoxy- or amino-substituted alkyl or alkoxy, represents alkenyl, alkenyloxy, alkinyl, respectively optionally substituted cycloalkyl or cycloalkylalkyl or respectively optionally substituted aryl, aryloxyalkyl or aralkyl, are obtained when hydrazine derivatives of the formula (IV)

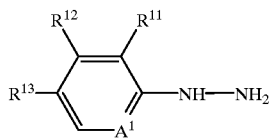
(IV)

in which

R$^{11}$, R$^{12}$, R$^{13}$, and A$^{1}$ are each as defined above are reacted with iminocarboxylic esters of the formula (V)

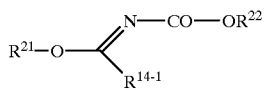
(V)

in which

R$^{14-1}$ is as defined above and

R$^{21}$ and R$^{22}$ independently of one another each represent alkyl (preferably C$_{1}$–C$_{8}$-alkyl) in the presence of a diluent; or c) N-aryl-1,2,4-triazolin-5-ones of the formula (Ic)

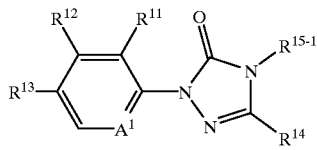
(Ic)

in which

R$^{11}$, R$^{12}$, R$^{13}$, R$^{14}$, and A$^{1}$ are each as defined above and R$^{15-1}$ represents cyano, optionally halogen-, cyano-, nitro-, alkoxy- or amino-substituted alkyl, represents alkenyl, alkinyl, respectively optionally substituted cycloalkyl and cycloalkylalkyl or optionally substituted aryl, are obtained when N-aryl-1,2,4-triazolin-5-ones of the formula (Id)

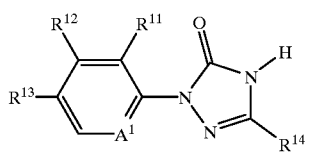
(Id)

in which

R$^{11}$, R$^{12}$, R$^{13}$, R$^{14}$, and A$^{1}$ are each as defined above are reacted with alkylating agents of the formula (VI)

E—R$^{15-1}$ (VI)

in which

R$^{15-1}$ is as defined above and

E represents an electron-withdrawing leaving group, if appropriate in the presence of a diluent and if appropriate in the presence of a reaction auxiliary.

A general definition of the novel N-aryl-1,2,4-triazolin-5-ones according to the invention is given by the formula (Ia).

Preferred substituents and ranges of the radicals listed in the formulae mentioned hereinabove and hereinbelow are illustrated in what follows.

$A^1$ preferably represents nitrogen or the group $CR^o$.

$R^o$ preferably represents hydrogen, fluorine, chlorine, bromine, nitro, cyano, hydroxyl, optionally fluorine-, chlorine-, cyano-, nitro- or $C_1$–$C_2$-alkoxy-substituted $C_1$–$C_4$-alkyl, optionally fluorine-, chlorine-, bromine-, $C_1$–$C_4$-alkyl-, $C_1$–$C_4$-alkoxy-, $C_1$–$C_4$-halogenoalkyl- or $C_1$–$C_4$-halogenoalkoxy-substituted $C_3$–$C_6$-cycloalkyl, or represents one of the radicals —$CONH_2$, —$CSNH_2$, —CO—NH—$C_1$–$C_4$-alkyl, —CS—NH—$C_1$–$C_4$-alkyl, —CO—N($C_1$–$C_4$-alkyl)$_2$, or —CS—N($C_1$–$C_4$-alkyl)$_2$.

$R^{11}$ preferably represents fluorine, chlorine, bromine, nitro, cyano, respectively optionally fluorine-, chlorine-, cyano-, nitro- or $C_1$–$C_2$-alkoxy-substituted $C_1$–$C_4$-alkyl or $C_1$–$C_4$-alkoxy, optionally fluorine-, chlorine-, bromine-, $C_1$–$C_4$-alkyl-, $C_1$–$C_4$-alkoxy-, $C_1$–$C_4$-halogenoalkyl- or $C_1$–$C_4$-halogenoalkoxy-substituted $C_3$–$C_6$-cycloalkyl, or represents one of the radicals —$CONH_2$, —$CSNH_2$, —CO—NH—$C_1$–$C_4$-alkyl, —CS—NH—$C_1$–$C_4$-alkyl, —CO—N($C_1$–$C_4$-alkyl)$_2$ or —CS—N($C_1$–$C_4$-alkyl)$_2$.

$R^{12}$ preferably represents hydrogen, fluorine, chlorine, $C_1$–$C_4$-alkyl or $C_1$–$C_4$-halogenoalkyl.

$R^{13}$ preferably represents nitro, $C_1$–$C_4$-halogenoalkyl, $C_1$–$C_4$-halogenoalkoxy or one of the radicals —S—$C_1$–$C_4$-halogenoalkyl, —SO—$C_1$–$C_4$-halogenoalkyl, or —$SO_2$—$C_1$–$C_4$-halogenoalkyl.

$R^{14}$ preferably represents halogen, cyano, respectively optionally fluorine-, chlorine-, cyano-, nitro-, $C_1$–$C_4$-alkoxy- or amino-substituted $C_1$–$C_4$-alkyl or $C_1$–$C_4$-alkoxy, represents $C_3$–$C_6$-alkenyl, $C_3$–$C_6$-alkenyloxy, $C_3$–$C_6$-alkinyl, hydroxyl, mercapto, respectively optionally fluorine-, chlorine-, bromine-, $C_1$–$C_4$-alkyl-, $C_1$–$C_4$-alkoxy-, $C_1$–$C_4$-halogenoalkyl- or $C_1$–$C_4$-halogenoalkoxy-substituted $C_3$–$C_6$-cycloalkyl, or $C_3$–$C_6$-cycloalkyl-$C_1$–$C_4$-alkyl, represents phenyl, phenyloxy-$C_1$–$C_4$-alkyl or phenyl-$C_1$–$C_4$-alkyl, each of which is optionally substituted by halogen, cyano, nitro, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy, $C_1$–$C_4$-halogenoalkylthio or optionally halogen- or $C_1$–$C_4$-alkyl-substituted phenyl, or represents the radical —$S(O)_n{}^1R^{16}$.

$R^{15}$ preferably represents hydrogen, cyano, amino, respectively optionally fluorine-, chlorine-, cyano-, nitro-, $C_1$–$C_4$-alkoxy- or amino-substituted $C_1$–$C_4$-alkyl or $C_1$–$C_4$-alkoxy, represents $C_3$–$C_6$-alkenyl, $C_3$–$C_6$-alkenyloxy, $C_3$–$C_6$-alkinyl, $C_3$–$C_6$-alkinyloxy, respectively optionally fluorine-, chlorine-, bromine-, $C_1$–$C_4$-alkyl-, $C_1$–$C_4$-alkoxy-, $C_1$–$C_4$-halogenoalkyl- or $C_1$–$C_4$-halogenoalkoxy-substituted $C_3$–$C_6$-cycloalkyl or $C_3$–$C_6$-cycloalkyl-$C_1$–$C_4$-alkyl, represents phenyl which is optionally substituted by halogen, cyano, nitro, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy, $C_1$–$C_4$-halogenoalkylthio or optionally halogen- or $C_1$–$C_4$-alkyl-substituted phenyl, represents optionally $C_1$–$C_4$-alkyl-substituted benzyl or one of the radicals —$S(O)_n{}^1R^{16}$, —$NR^{17}R^{18}$ or —N=$CR^{19}R^{20}$.

$R^{16}$ preferably represents optionally fluorine-, chlorine-, cyano- or nitro-substituted $C_1$–$C_4$-alkyl, represents $C_3$–$C_6$-alkenyl, $C_3$–$C_6$-alkanedienyl, $C_3$–$C_6$-alkinyl, optionally fluorine-, chlorine-, bromine-, $C_1$–$C_4$-alkyl-, $C_1$–$C_4$-alkoxy-, $C_1$–$C_4$-halogenoalkyl- or $C_1$–$C_4$-halogenoalkoxy-substituted $C_3$–$C_6$-cycloalkyl, or phenyl which is optionally substituted by halogen, cyano, nitro, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy, $C_1$–$C_4$-halogenoalkylthio or optionally halogen- or $C_1$–$C_4$-alkyl-substituted phenyl.

$n^1$ preferably represents one of the numbers 0, 1 or 2.

$R^{17}$ and $R^{18}$ preferably join with the linking nitrogen atom to represent an optionally halogen-, $C_1$–$C_4$-alkyl-, $C_1$–$C_4$-alkoxy- or $C_1$–$C_4$-alkylthio-substituted saturated 5- to 7-membered heterocycle having, in addition to the nitrogen atom, 2 or 3 identical or different hetero atoms from the group consisting of nitrogen, oxygen and sulphur.

$R^{19}$ preferably represents hydrogen, optionally fluorine-, chlorine-, cyano-, nitro-, amino- or $C_1$–$C_4$-alkoxy-substituted $C_1$–$C_4$-alkyl or represents $C_1$–$C_4$-alkoxy.

$R^{20}$ preferably represents hydrogen, optionally fluorine-, chlorine-, cyano-, nitro-, amino- or $C_1$–$C_4$-alkoxy-substituted $C_1$–$C_4$-alkyl or represents $C_1$–$C_4$-alkoxy.

$A^1$ particularly preferably represents nitrogen or the group $CR^o$.

$R^o$ particularly preferably represents hydrogen, fluorine, chlorine, bromine, nitro, cyano, hydroxyl, methyl, ethyl, n- or i-propyl, methoxymethyl, trifluoromethyl, difluoromethyl, chlorodifluoromethyl, dichlorofluoromethyl or represents one of the radicals —$CONH_2$, —$CSNH_2$, —$CONHCH_3$, —$CSNHCH_3$, —$CON(CH_3)_2$ or —$CSN(CH_3)_2$.

$R^{11}$ particularly preferably represents fluorine, chlorine, bromine, nitro, cyano, methyl, ethyl, n- or i-propyl, methoxymethyl, trifluoromethyl, difluoromethyl, chlorodifluoromethyl, dichlorofluoromethyl, trifluoromethoxy, difluoromethoxy, trifluoroethoxy or one of the radicals —$CONH_2$, —$CSNH_2$, —$CONHCH_3$, —$CSNHCH_3$, —$CON(CH_3)_2$ and —$CSN(CH_3)_2$.

$R^{12}$ particularly preferably represents hydrogen, fluorine, chlorine, methyl or trifluoromethyl.

$R^{13}$ particularly preferably represents trifluoromethyl, difluoromethyl, chlorodifluoromethyl, dichlorofluoromethyl, trifluoromethoxy, difluoromethoxy, chlorodifluoromethoxy, trifluoromethylsulphenyl, trifluoromethylsulphinyl or trifluoromethylsulphonyl.

$R^{14}$ particularly preferably represents chlorine, bromine, cyano, methyl, ethyl, n- or i-propyl, n-, i-, s- or t-butyl, methoxy, ethoxy, n- or i-propoxy, n-, i-, s- or t-butoxy, methoxymethyl, methoxyethyl, ethoxymethyl, ethoxyethyl, trifluoromethyl, difluoromethyl, chlorodifluoromethyl, dichlorofluoromethyl, trifluoroethyl, tetrafluoroethyl, pentafluoroethyl, fluoropropyl, trifluoromethoxy, difluoromethoxy, chlorodifluoromethoxy, dichlorofluoromethoxy, trifluoroethoxy, tetrafluoroethoxy, pentafluoroethoxy, cyanomethyl, allyl, allyloxy, propargyl, hydroxyl, mercapto, respectively optionally fluorine-, chlorine-, bromine-, methyl-, ethyl-, methoxy-, trifluoromethyl- or trifluoromethoxy-substituted cyclopropyl, cyclopropylmethyl, cyclopentyl, cyclopentylmethyl, cyclohexyl or cyclohexylmethyl, represents phenyl, phenoxymethyl or benzyl, each of which is optionally substituted by fluorine, chlorine, methyl, methoxy, trifluoromethyl, trifluoromethoxy, methylthio, trifluoromethylthio, nitro, or optionally fluorine-, chlorine- or methyl-substituted phenyl, or represents the radical —$S(O)_n{}^1R^{16}$.

$R^{15}$ particularly preferably represents hydrogen, cyano, amino, methyl, ethyl, n- or i-propyl, n-, i-, s- or t-butyl, methoxy, ethoxy, n- or i-propoxy, n-, i-, s- or t-butoxy, methoxymethyl, methoxyethyl, ethoxymethyl, ethoxyethyl, difluoromethyl, chlorodifluoromethyl, dichlorofluoromethyl, trifluoroethyl, fluoropropyl, difluoromethoxy, chlorodifluoromethoxy, dichlorofluoromethoxy, cyanomethyl, allyl, allyloxy, propargyl, propargyloxy, butinyloxy, respectively optionally fluorine-, chlorine-, bromine-, methyl-, ethyl-, methoxy-, trifluoromethyl- or trifluoromethoxy-substituted cyclopropyl, cyclopropylmethyl, cyclopentyl, cyclopentylmethyl, cyclohexyl or cyclohexylmethyl, represents phenyl which is optionally substituted by fluorine, chlorine, methyl, methoxy, trifluoromethyl, trifluoromethoxy, methylthio, trifluoromethylthio, cyano, nitro, or optionally fluorine-, chlorine- or methyl-substituted phenyl, represents optionally methyl-, ethyl-, n- or i- propyl-, n-, i-, s- or t-butyl-substituted benzyl or represents one of the radicals —S(O)$_{n^1}$R$^{16}$, NR$^{17}$R$^{18}$ or —N═CR$^{19}$R$^{20}$.

$R^{16}$ particularly preferably represents methyl, ethyl, n- or i-propyl, n-, i-, s- or t-butyl, trifluoromethyl, difluoromethyl, chlorodifluoromethyl, dichlorofluoromethyl, trifluoroethyl, tetrafluoroethyl, pentafluoroethyl, fluoropropyl, allyl, allenyl, propargyl, respectively optionally fluorine-, chlorine-, bromine-, methyl-, ethyl-, methoxy-, trifluoromethyl- or trifluoromethoxy-substituted cyclopropyl, cyclopentyl or cyclohexyl, or phenyl which is optionally substituted by fluorine, chlorine, methyl, methoxy, trifluoromethyl, trifluoromethoxy, methylthio, trifluoromethylthio, cyano, nitro, or optionally fluorine-, chlorine- or methyl-substituted phenyl.

$n^1$ particularly preferably represents one of the numbers 0, 1 or 2.

$R^{17}$ and $R^{18}$ particularly preferably join with the linking nitrogen atom to represent respectively optionally methyl-, ethyl-, methoxy- or ethoxy-substituted piperidinyl, piperazinyl or morpholinyl.

$R^{19}$ particularly preferably represents hydrogen, methyl, ethyl, n- or i-propyl, n-, i-, s- or t-butyl, -methoxy or ethoxy.

$R^{20}$ particularly preferably represents hydrogen, methyl, ethyl, n- or i-propyl, n-, i-, s- or t-butyl, methoxy or ethoxy.

The abovementioned radical definitions or illustrations mentioned generally or in preferred ranges apply to the end products and, correspondingly, to the starting materials and intermediates. These radical definitions can be combined with each other as desired, i.e. including between the respective preferred ranges.

According to the invention, preference is given to compounds of the formula (I) in which there exists a combination of the meanings mentioned above as preferred (preferable).

According to the invention, particular preference is given to compounds of the formula (I) in which there exists a combination of the meanings mentioned above as particularly preferred.

Hydrocarbon radicals such as alkyl or alkenyl mentioned in the radical definitions hereinabove and hereinbelow are, as far as possible, in each case straight-chain or branched, including in conjunctions with hetero atoms, e.g. alkoxy or alylthio.

Examples of the novel compounds according to the invention are listed in Tables 1a to 80d:

TABLE 1a

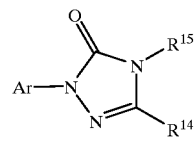

(IA)

Compounds of Table 1a correspond to the general formula (IA) in which
$R^{14}$ = $CH_3$
$R^{15}$ = $CH_3$ and
Ar = as listed below:

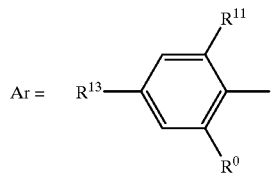

| $R^{11}$ | $R^{13}$ | $R^0$ |
|---|---|---|
| Cl | $CF_3$ | Cl |
| F | $CF_3$ | Cl |
| Br | $CF_3$ | Cl |
| F | $CF_3$ | F |
| Br | $CF_3$ | F |
| Cl | $CF_3$ | CN |
| Br | $CF_3$ | CN |
| F | $CF_3$ | CN |
| $NO_2$ | $CF_3$ | CN |
| $NO_2$ | $CF_3$ | $NO_2$ |
| $NO_2$ | $CF_3$ | Cl |
| $NO_2$ | $CF_3$ | Br |
| $NO_2$ | $CF_3$ | F |
| $CF_3$ | $CF_3$ | $CF_3$ |
| $CF_3$ | $CF_3$ | Cl |
| CN | $CF_3$ | CN |
| Cl | $CF_3$ | $CH_3$ |
| Cl | $CF_3$ | $C_2H_5$ |
| Cl | —$OCF_3$ | Cl |
| F | —$OCF_3$ | Cl |
| Cl | —$OCHF_2$ | Cl |
| Cl | $CF_3$ | —$CSNH_2$ |
| F | $CF_3$ | —$CSNH_2$ |
| Br | $CF_3$ | —$CSNH_2$ |
| Cl | $CF_3$ | —$CSNHCH_3$ |
| Cl | $CF_3$ | —$CSN(CH_3)_2$ |
| —$CONH_2$ | $CF_3$ | Cl |
| F | —$OCHF_2$ | —$CSNH_2$ |
| Cl | —$OCF_3$ | —$CSNH_2$ |
| Br | —$OCF_3$ | —$CSNH_2$ |
| Br | $CF_3$ | —$CSNHCH_3$ |
| F | $CF_3$ | —$CSNHCH_3$ |
| F | $CF_3$ | —$CSN(CH_3)_2$ |
| Br | $CF_3$ | —$CSN(CH_3)_2$ |
| CN | $CF_3$ | —$CSN(CH_3)_2$ |
| —$CONHCH_3$ | $CF_3$ | Cl |
| —$CON(CH_3)_2$ | $CF_3$ | Cl |
| F | $CF_3$ | —$CONH_2$ |
| F | $CF_3$ | —$CONHCH_3$ |
| F | $CF_3$ | —$CON(CH_3)_2$ |
| F | —$OCF_3$ | —$CSNH_2$ |
| F | —$OCF_3$ | —$CONH_2$ |
| Cl | —$SO_2CF_3$ | F |
| Cl | —$SO_2CF_3$ | Cl |
| Cl | —$SO_2CF_3$ | $NO_2$ |
| Cl | —$SO_2CF_3$ | CN |
| Cl | —$SO_2CF_3$ | —$CONH_2$ |
| Cl | —$SO_2CF_3$ | —$CSNH_2$ |
| Cl | —$SO_2CF_3$ | —$CSNHCH_3$ |
| Cl | —$SO_2CF_3$ | —$CSN(CH_3)_2$ |
| Cl | —$SO_2CF_3$ | —$CONHCH_3$ |

TABLE 1a-continued

| | | |
|---|---|---|
| Cl | —SO$_2$CF$_3$ | —CON(CH$_3$)$_2$ |
| Cl | —SCF$_3$ | Cl |
| Cl | —SOCF$_3$ | Cl |

TABLE 1b

Table 1b contains the compounds of the general formula (IA) in which
R$^{14}$ = CH$_3$
R$^{15}$ = CH$_3$ and
Ar = as listed below:

Ar = 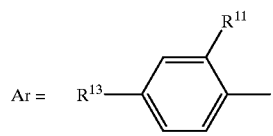

| R$^{11}$ | R$^{13}$ |
|---|---|
| CN | CF$_3$ |
| Cl | CF$_3$ |
| Cl | —OCF$_3$ |
| Cl | —OCClF$_2$ |

TABLE 1c

Table 1c contains the compounds of the general formula (IA) in which
R$^{14}$ = CH$_3$
R$^{15}$ = CH$_3$ and
Ar = as listed below:

Ar = 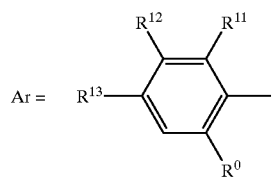

| R$^{11}$ | R$^{12}$ | R$^{13}$ | R$^0$ |
|---|---|---|---|
| Cl | F | CF$_3$ | Cl |
| Cl | F | CF$_3$ | F |

TABLE 1d

Table 1d contains the compounds of the general formula (IA) in which
R$^{14}$ = CH$_3$
R$^{15}$ = CH$_3$ and
Ar = as listed below:

Ar = 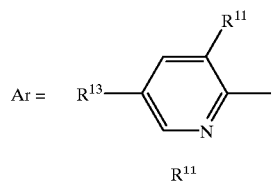

| R$^{11}$ | R$^{13}$ |
|---|---|
| Cl | CF$_3$ |
| F | CF$_3$ |

TABLES 2a TO 2d

Tables 2a to 2d contain the compounds of the general formula (IA) in which
R$^{14}$=C$_2$H$_5$
R$^{15}$=CH$_3$ and
Ar=as listed in Tables 1a to 1d.

TABLES 3a TO 3d

Tables 2a to 2d contain the compounds of the general formula (IA) in which
R$^{14}$=C$_3$H$_7$-i
R$^{15}$=CH$_3$ and
Ar=as listed in Tables 1a to 1d.

TABLES 4a TO 4d

Tables 4a to 4d contain the compounds of the general formula (IA) in which
R$^{14}$=C$_3$H$_7$-n
R$^{15}$=CH$_3$ and
Ar=as listed in Tables 1a to 1d.

TABLES 5a TO 5d

Tables 5a to 5d contain the compounds of the general formula (IA) in which
R$^{14}$=C$_4$H$_9$-n
R$^{15}$=CH$_3$ and
Ar=as listed in Tables 1a to 1d.

TABLES 6a TO 6d

Tables 6a to 6d contain the compounds of the general formula (IA) in which

R$^{14}$ = 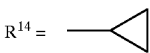

R$^{15}$=CH$_3$ and
Ar=as listed in Tables 1a to 1d.

TABLES 7a TO 7d

Tables 7a to 7d contain the compounds of the general formula (IA) in which

R$^{14}$ = 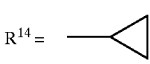

R$^{15}$=C$_2$H$_5$ and
Ar=as listed in Tables 1a to 1d.

TABLES 8a TO 8d

Tables 8a to 8d contain the compounds of the general formula (IA) in which

R$^{14}$ = 

R$^{15}$=C$_3$H$_7$-i and
Ar=as listed in Tables 1a to 1d.

TABLES 9a TO 9d

Tables 9a to 9d contain the compounds of the general formula (IA) in which $R^{14}$ = 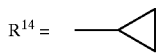

$R^{15}$ = 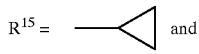 and

Ar=as listed in Tables 1 to 1d.

TABLES 10a TO 10d

Tables 10a to 10d contain the compounds of the general formula (IA) in which
$R^{14}$=C$_3$H$_7$-i $R^{15}$ = 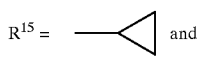 and Ar=as listed in Tables 1a to 1d.

TABLES 11a TO 11d

Tables 11a to 1d contain the compounds of the general formula (IA) in which
$R^{14}$=C$_4$H$_9$-t $R^{15}$ = 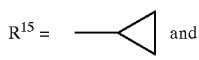 and Ar=as listed in Tables 1a to 1d.

TABLES 12a TO 12d

Tables 12a to 12d contain the compounds of the general formula (IA) in which $R^{14}$ = 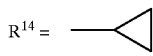

$R^{15}$=—CH$_2$CH$_2$OCH$_3$ and
Ar as listed in Tables 1a to 1d.

TABLES 13a TO 13d

Tables 13a to 13d contain the compounds of the general formula (IA) in which
$R^{14}$=CF$_3$
$R^{15}$=H and
Ar=as listed in Tables 1a to 1d.

TABLES 14a TO 14d

Tables 14a to 14d contain the compounds of the general formula (IA) in which
$R^{14}$ CF$_3$
$R^{15}$=—SCFCl$_2$ and
Ar=as listed in Tables 1a to 1d.

TABLES 15a TO 15d

Tables 15a to 15d contain the compounds of the general formula (IA) in which $R^{14}$ = 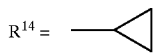

$R^{15}$=—OCH$_3$ and
Ar=as listed in Tables 1a to 1d.

TABLES 16a TO 16d

Tables 16a to 16d contain the compounds of the general formula (IA) in which $R^{14}$ = 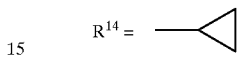

$R^{15}$=—OC$_2$H$_5$ and
Ar=as listed in Tables 1a to 1d.

TABLES 17a TO 17d

Tables 17a to 17d contain the compounds of the general formula (IA) in which $R^{14}$ = 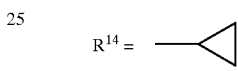

$R^{15}$=—OCH$_2$CH=CH$_2$ and
Ar=as listed in Tables 1a to 1d.

TABLES 18a TO 18d

Tables 18a to 18d contain the compounds of the general formula (IA) in which $R^{14}$ = 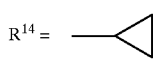

$R^{15}$=—NH$_2$ and
Ar=as listed in Tables 1a to 1d.

TABLES 19a TO 19d

Tables 19a to 19d contain the compounds of the general formula (IA) in which $R^{14}$ = 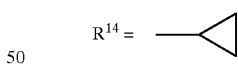

$R^{15}$=—CHF$_2$ and
Ar=as listed in Tables 1a to 1d.

TABLES 20a TO 20d

Tables 20a to 20d contain the compounds of the general formula (IA) in which
$R^{14}$=CF$_3$
$R^{15}$=C$_3$H$_7$-i and
Ar=as listed in Tables 1a to 1d.

TABLES 21a TO 21d

Tables 21a to 21d contain the compounds of the general formula (IA) in which
$R^{14}$=CHF$_3$ $R^{15}=CH_3$ and
Ar=as listed in Tables 1a to 1d.

TABLES 22a TO 22d

Tables 22a to 22d contain the compounds of the general formula (IA) in which
$R^{14}=CF_3$
$R^{15}=CH_2H_5$ and
Ar=as listed in Tables 1a to 1d.

TABLES 23a TO 23d

Tables 23a to 23d contain the compounds of the general formula (IA) in which
$R^{14}=CF_3$
$R^{15}=C_4H_9$-t and
Ar=as listed in Tables 1a to 1d.

TABLES 24a TO 24d

Tables 24a to 24d contain the compounds of the general formula (IA) in which
$R^{14}=CF_3$

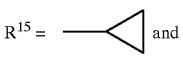

Ar=as listed in Tables 1a to 1d.

TABLES 25a To 25d

Tables 25a to 25d contain the compounds of the general formula (IA) in which
$R^{14}=CF_3$

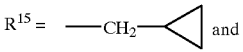

Ar=as listed in Tables 1a to 1d.

TABLES 26a TO 26d

Tables 26a to 26d contain the compounds of the general formula (IA) in which
$R^{14}=CHF_2$

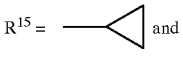

Ar=as listed in Tables 1a to 1d.

TABLES 27a TO 27d

Tables 27a to 27d contain the compounds of the general formula (IA) in which
$R^{14}=CHF_2$
$R^{15}=CN$ and
Ar=as listed in Tables 1a to 1d.

TABLES 28a TO 28d

Tables 28a to 28d contain the compounds of the general formula (IA) in which
$R^{14}=CF_3$
$R^{15}=CN$ and
Ar=as listed in Tables 1a to 1d.

TABLES 29a TO 29d

Tables 29a to 29d contain the compounds of the general formula (IA) in which
$R^{14}=SCHF_2$
$R^{15}=-C_3H_7$-i and
Ar=as listed in Tables 1a to 1d.

TABLES 30a TO 30d

Tables 30a to 30d contain the compounds of the general formula (IA) in which
$R^{14}=CF_3$
$R^{15}=-OCH_3$ and
Ar=as listed in Tables 1a to 1d.

TABLES 31a TO 31d

Tables 31 a to 31d contain the compounds of the general formula (IA) in which
$R^{14}=CF_3$
$R^{15}=-CH_2CH_2OCH_3$ and
Ar=as listed in Tables 1a to 1d.

TABLES 32a TO 32d

Tables 32a to 32d contain the compounds of the general formula (IA) in which
$R^{14}=CF_3$

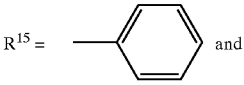

Ar=as listed in Tables 1a to 1d.

TABLES 33a TO 33d

Tables 33a to 33d contain the compounds of the general formula (IA) in which
$R^{14}=CF_3$

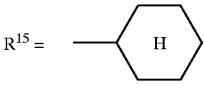

Ar=as listed in Tables 1a to 1d.

TABLES 34a TO 34d

Tables 34a to 34d contain the compounds of the general formula (IA) in which
$R^{14}=CF_3$

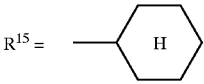

and
Ar=as listed in Tables 1a to 1d.

TABLES 35a TO 35d

Tables 35a to 35d contain the compounds of the general formula (IA) in which $R^{14}$=—OCH$_2$CF$_3$

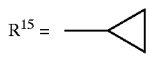

and
Ar=as listed in Tables 1a to 1d.

TABLES 36a TO 36d

Tables 36a to 36d contain the compounds of the general formula (IA) in which

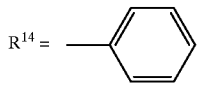

Ar=as listed in Tables 1a to 1d.

TABLES 37a TO 37d

Tables 37a to 37d contain the compounds of the general formula (IA) in which
$R^{14}$=—CF$_2$CF$_3$

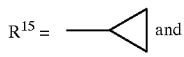

and
Ar=as listed in Tables 1a to 1d.

TABLES 38a TO 38d

Tables 38a to 38d contain the compounds of the general formula (IA) in which
$R^{14}$=—CF$_2$CF$_3$
$R^{15}$=C$_4$H$_9$-t and
Ar=as listed in Tables 1a to 1d.

TABLES 39a TO 39d

Tables 39a to 39d contain the compounds of the general formula (IA) in which
$R^{14}$=—CF$_2$CF$_3$
$R^{15}$=C$_3$H$_7$-i and
Ar=as listed in Tables 1a to 1d.

TABLES 40a to 40d

Tables 40a to 40d contain the compounds of the general formula (IA) in which
$R^{14}$=—CF$_2$CF$_3$
$R^{15}$=C$_2$H$_5$ and
Ar=as listed in Tables 1a to 1d.

TABLES 41a to 41d

Tables 41a to 41d contain the compounds of the general formula (IA) in which
$R^{14}$=—CF$_2$CF$_3$
$R^{15}$=CH$_3$ and
Ar=as listed in Tables 1a to 1d.

TABLES 42a to 42d

Tables 42a to 42d contain the compounds of the general formula (IA) in which
$R^{14}$=—CF$_2$CHF$_2$
$R^{15}$=CH$_3$ and
Ar=as listed in Tables 1a to 1d.

TABLES 43a TO 43d

Tables 43a to 43d contain the compounds of the general formula (IA) in which
$R^{14}$=—CF$_2$CHF$_2$
$R^{15}$=C$_2$H$_5$ and
Ar=as listed in Tables 1a to 1d.

TABLES 44a TO 44d

Tables 44a to 44d contain the compounds of the general formula (IA) in which
$R^{14}$=—CF$_2$CHF$_2$
$R^{15}$=C$_3$H$_7$-i and
Ar=as listed in Tables 1a to 1d.

TABLES 45a TO 45d

Tables 45a to 45d contain the compounds of the general formula (IA) in which
$R^{14}$=—CF$_2$CHF$_2$
$R^{15}$=C$_3$H$_9$-t and
Ar=as listed in Tables 1a to 1d.

TABLES 46a TO 46d

Tables 46a to 46d contain the compounds of the general formula (IA) in which
$R^{14}$=—CF$_2$CHF$_2$
$R^{15}$=C$_3$H$_7$-n and
Ar=as listed in Tables 1a to 1d.

TABLES 47a TO 47d

Tables 47a to 47d contain the compounds of the general formula (IA) in which
$R^{14}$=—CF$_2$CHF$_2$

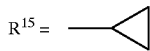

and
Ar=as listed in Tables 1a to 1d.

TABLES 48a TO 48d

Tables 48a to 48d contain the compounds of the general formula (IA) in which
$R^{14}$=CF$_3$
$R^{15}$=—CH$_2$CH$_2$CH$_2$F and
Ar=as listed in Tables 1a to 1d.

TABLES 49a TO 49d

Tables 49a to 49d contain the compounds of the general formula (IA) in which
$R^{14}$=—C$_3$H$_7$-i
$R^{15}$=—CH$_2$CH$_2$CH$_2$F and Ar=as listed in Tables 1a to 1d.

TABLES 50a TO 50d

Tables 50a to 50d contain the compounds of the general formula (IA) in which $R^{14} =$ 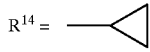

$R^{15}$ —$CH_2CH_2CH_2F$ and
Ar=as listed in Tables 1a to 1d.

TABLES 51a TO 51d

Tables 51a to 51d contain the compounds of the general formula (IA) in which
$R^{14}$=CN
$R^{15}$=—$CH_2CH_2CH_2F$ and
Ar=as listed in Tables 1a to 1d.

TABLES 52a TO 52d

Tables 52a to 52d contain the compounds of the general formula (IA) in which
$R^{14}$=CN
$R^{15}$=—$CHF_2$ and
Ar=as listed in Tables 1a to 1d.

TABLES 53a TO 13d

Tables 53a to 13d contain the compounds of the general formula (IA) in which
$R^{14}$=CN $R^{15} =$ 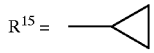

and
Ar=as listed in Tables 1a to 1d.

TABLES 54a TO 54d

Tables 54a to 54d contain the compounds of the general formula (IA) in which
$R^{14}$=Br $R^{15} =$ 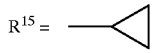

and
Ar=as listed in Tables 1a to 1d.

TABLES 55a TO 55d

Tables 55a to 55d contain the compounds of the general formula (IA) in which
$R^{14}$=Cl $R^{15} =$ 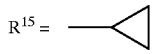

and
Ar=as listed in Tables 1a to 1d.

TABLES 56a TO 56d

Tables 56a to 56d contain the compounds of the general formula (IA) in which
$R^{14}$=Cl
$R^{15}$=—$CHF_2$ and
Ar=as listed in Tables 1a to 1d.

TABLES 57a TO 57d

Tables 57a to 57d contain the compounds of the general formula (IA) in which
$R^{14}$=Cl
$R^{15}$=—$CH_3$ and
Ar=as listed in Tables 1a to 1d.

TABLES 58a TO 58d

Tables 58a to 58d contain the compounds of the general formula (IA) in which
$R^{14}$=Cl
$R^{15}$=—$C_2H_5$ and
Ar as listed in Tables 1a to 1d.

TABLES 59a TO 59d

Tables 59a to 59d contain the compounds of the general formula (IA) in which
$R^{14}$=Cl
$R^{15}$=—$C_3H_7$-i and
Ar as listed in Tables 1a to 1d.

TABLES 60a TO 60d

Tables 60a to 60d contain the compounds of the general formula (IA) in which
$R^{14}$=Br
$R^{15}$=—$C_3H_7$-i and
Ar=as listed in Tables 1a to 1d.

TABLES 61a TO 61d

Tables 61a to 61d contain the compounds of the general formula (IA) in which
$R^{14}$=Br
$R^{15}$=—$C_4H_9$-t and
Ar=as listed in Tables 1a to 1d.

TABLES 62a TO 62d

Tables 62a to 62d contain the compounds of the general formula (IA) in which
$R^{14}$=$SCHF_2$ $R^{15} =$ 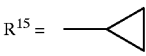

and
Ar=as listed in Tables 1a to 1d.

TABLES 63a TO 63d

Tables 63a to 63d contain the compounds of the general formula (IA) in which $R^{14}$=OCF$_2$H $R^{15}=$ 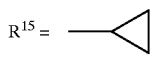

and

Ar=as listed in Tables 1a to 1d.

TABLES 64a TO 64d

Tables 64a to 64d contain the compounds of the general formula (IA) in which
$R^{14}$=OCHF$_2$
$R^{15}$=C$_4$H$_9$-t and
Ar=as listed in Tables 1a to 1d.

TABLES 65a TO 65d

Tables 65a to 65d contain the compounds of the general formula (IA) in which
$R^{14}$=—OCH$_3$ $R^{15}=$ 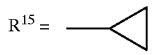

and

Ar=as listed in Tables 1a to 1d.

TABLES 66a TO 66d

Tables 66a to 66d contain the compounds of the general formula (IA) in which
$R^{14}$=—OC$_2$H$_5$ $R^{15}=$ 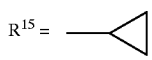

and

Ar=as listed in Tables 1a to 1d.

TABLES 67a TO 67d

Tables 67a to 67d contain the compounds of the general formula (IA) in which
$R^{14}$=—OC$_3$H$_7$-i $R^{15}=$ 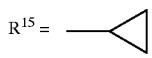

and

Ar=as listed in Tables 1a to 1d.

TABLES 68a TO 68d

Tables 68a to 68d contain the compounds of the general formula (IA) in which
$R^{14}$=—SCH$_3$ $R^{15}=$ 

and

Ar=as listed in Tables 1a to 1d.

TABLES 69a TO 69d

Tables 69a to 69d contain the compounds of the general formula (IA) in which
$R^{14}$=—SO$_2$CH$_3$ $R^{15}=$ 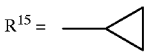

and

Ar as listed in Tables 1a to 1d.

TABLES 70a TO 70d

Tables 70a to 70d contain the compounds of the general -formula (IA) in which
$R^{14}$=—SC$_3$H$_7$-i $R^{15}=$ 

and

Ar=as listed in Tables 1a to 1d.

TABLES 71a TO 71d

Tables 71a to 71d contain the compounds of the general formula (IA) in which
$R^{14}$=C$_4$H$_9$-t
$R^{15}$=CN and
Ar=as listed in Tables 1a to 1d.

TABLES 72a TO 72d

Tables 72a to 72d contain the compounds of the general formula (IA) in which
$R^{14}$=—SC$_2$H$_5$
$R^{15}$=—CN and
Ar=as listed in Tables 1a to 1d.

TABLES 73a TO 73d

Tables 73a to 73d contain the compounds of the general formula (IA) in which
$R^{14}$=CF$_3$
$R^{15}$=—CHF$_2$ and
Ar=as listed in Tables 1a to 1d.

TABLES 74a TO 74d

Tables 74a to 74d contain the compounds of the general formula (IA) in which
$R^{14}$=CF$_3$
$R^{15}$=—CH$_2$CN and
Ar=as listed in Tables 1a to 1d.

TABLES 75a TO 75d

Tables 75a to 75d contain the compounds of the general formula (IA) in which $R^{14}=CF_3$

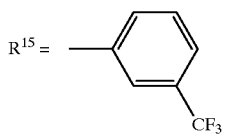

$R^{15}=$ and
Ar=as listed in Tables 1a to 1d.

TABLES 76a TO 76d

Tables 76a to 76d contain the compounds of the general formula (IA) in which
$R^{14}=CF_3$

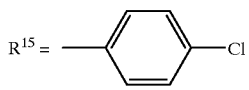

$R^{15}=$ and
Ar=as listed in Tables 1a to 1d.

TABLES 77a TO 77d

Tables 77a to 77d contain the compounds of the general formula (IA) in which
$R^{14}=CF_3$
$R^{15}=$—N=CHOC$_2$C$_5$ and
Ar=as listed in Tables 1a to 1d.

TABLES 78a TO 78d

Tables 78a to 78d contain the compounds of the general formula (IA) in which
$R^{14}=CF_3$

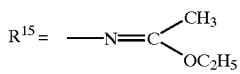

$R^{15}=$ and
Ar=as listed in Tables 1a to 1d.

TABLES 79a TO 79d

Tables 19a to 19d contain the compounds of the general formula (IA) in which
$R^{14}=CF_3$

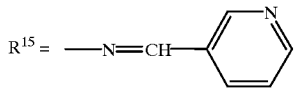

$R^{15}=$ and
Ar=as listed in Tables 1a to 1d.

TABLES 80a TO 80d

Tables 80a to 80d contain the compounds of the general formula (IA) in which
$R^{14}=CF_3$
$R^5=$—SO$_2$CF$_2$CH$_3$ and
Ar=as listed in Tables 1a to 1d.

If for example 2,6-dichloro-4-trifluoromethyl-fluorobenzene and 3-cyano-4-cyclopropyl-1H-1,2,4-triazolin-5-one are used as starting materials, the course of the process (a) according to the invention can be represented by the following scheme:

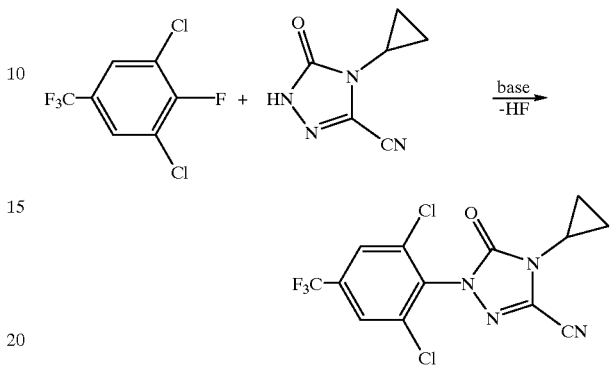

If for example 2,6-dinitro-4-trifluoromethyl-phenyl-hydrazine and N-methoxycarbonyl-acetimidate are used as starting materials, the course of the process (b) according to the invention can be represented by the following scheme:

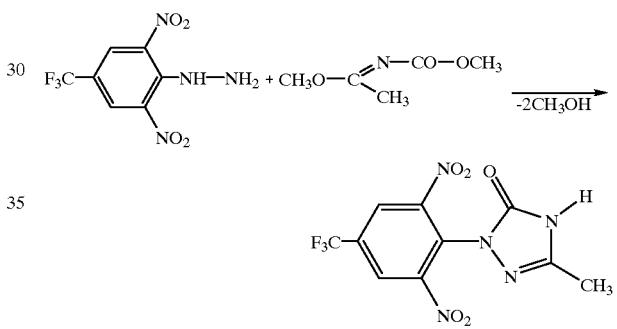

If for example 1-(2,6-dichloro-4-trifluoromethyl-phenyl)-3-methyl-(4H)-1,2,4-triazolin-5-one and chlorodifluoromethane are used as starting materials, the course of the process (c) according to the invention can be represented by the following scheme:

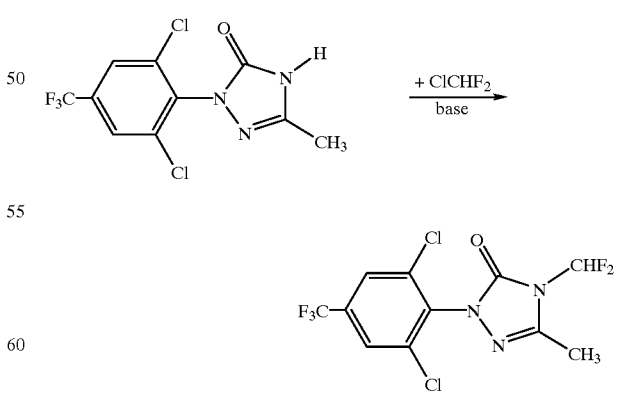

The formula (II) provides a general definition of the 1H-triazolinones required as starting materials for carrying out the process (a) according to the invention. In this formula (II), $R^{14}$ and $R^{15}$ each preferably and in particular represent those radicals which have already been mentioned in connection with the description of the compounds of the formula (Ia) according to the invention as preferred or particularly preferred for these substituents.

The 1H-triazolinones of the formula (II) are known or obtainable by known processes (cf. for example EP 283 876; EP 305 844; EP 341 489; EP 415 196; EP 422 469; EP 425 948; EP 431 291; EP 507 171; EP 513 621; EP 534 266; Chem. Ber. 102, 755–766 [1969]; Liebigs Ann. Chem. 343, 24 [1905]). Some of them also form part of the subject-matter of a commonly assigned, hitherto unpublished patent application (cf. German Patent Application P 4 435 547 05.10.1994).

Examples of the 1H-triazolinones of the formula (II) are listed in Tables (II-1) to (II-49):

TABLE (II-1)

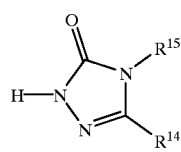

(II)

The compounds of Table (II-1) correspond to the general formula (II) in which $R^{14}$=CH$_3$ and
$R^{15}$=as listed below:

H, CH$_3$, C$_2$H$_5$, n-C$_3$H$_7$, i-C$_3$H$_7$, n-C$_4$H$_9$, i-C$_4$H$_9$, s-C$_4$H$_9$, t-C$_4$H$_9$, CHF$_2$, CClF$_2$, CHClF, CH$_2$CH$_2$CH$_2$F, CH$_2$CF$_3$, CHF=CClF, CH$_2$CH$_2$—O—CH$_3$, CH$_2$CH$_2$—O—CH$_2$CH$_3$, CH$_2$CH=CH$_2$, CH$_2$CH$_2$CH$_2$—O—CH$_3$, CH$_2$CN, CN, CH$_2$C≡CH, O—CH$_3$, O—C$_2$H$_5$, O—CH$_2$CH=CH$_2$, O—CH(CH$_3$)C≡CH, SCFCl$_2$, SO$_2$CF$_2$CH$_3$, N=CHOC$_2$H$_5$, N=C(CH$_3$)OC$_2$H$_5$, NH$_2$,

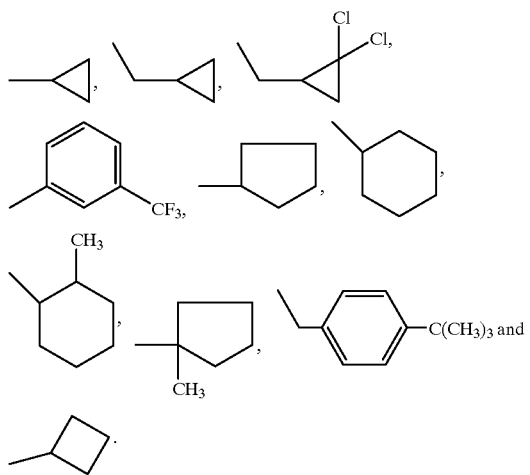

TABLE (II-2)

Table (II-2) contains the compounds of the general formula (II) in which
$R^{14}$=C$_2$H$_5$ and
$R^{15}$=as listed in Table (II-1).

TABLE (II-3)

Table (II-3) contains the compounds of the general formula (II) in which $R^{14}$=C$_3$H$_7$-i and
$R^{15}$=as listed in Table (II-1).

TABLE (II-4)

Table (II-4) contains the compounds of the general formula (II) in which
$R^{14}$=C$_3$H$_7$-n and
$R^{15}$=as listed in Table (II-1).

TABLE (II-5)

Table (II-5) contains the compounds of the general formula (II) in which
$R^{14}$=C$_4$H$_9$-n and
$R^{15}$=as listed in Table (II-1).

TABLE (II-6)

Table (II-6) contains the compounds of the general formula (II) in which
$R^{14}$=C$_4$H$_9$-i and
$R^{15}$=as listed in Table (II-1).

TABLE (II-7)

Table (II-7) contains the compounds of the general formula (II) in which
$R^{14}$=C$_4$H$_9$-t and
$R^{15}$=as listed in Table (II-1).

TABLE (II-8)

Table (II-8) contains the compounds of the general formula (II) in which
$R^{14}$=C$_4$H$_9$-s and
$R^{15}$=as listed in Table (II-1).

TABLE (II-9)

Table (II-9) contains the compounds of the general formula (II) in which $R^{14}$ = 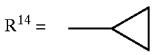

and
$R^{15}$=as listed in Table (II-1).

TABLE (II-10)

Table (II-10) contains the compounds of the general formula (II) in which
$R^{14}$=CF$_3$ and
$R^{15}$=as listed in Table (II-1).

TABLE (II-11)

Table (II-11) contains the compounds of the general formula (II) in which
$R^{14}$=CHF$_2$ and
$R^{15}$ as listed in Table (II-1).

TABLE (II-12)

Table (II-12) contains the compounds of the general formula (II) in which
$R^{14}$=CClF$_2$ and $R^{15}$=as listed in Table (II-1).

TABLE (II-13)

Table (II-13) contains the compounds of the general formula (II) in which
$R^{14}=CF_2CF_3$ and
$R^{15}$=as listed in Table (II-1).

TABLE (II-14)

Table (II-14) contains the compounds of the general formula (II) in which
$R^{14}=CF_2CHF_2$ and
$R^{15}$=as listed in Table (II-1).

TABLE (II-15)

Table (II-15) contains the compounds of the general formula (II) in which

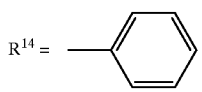

and
$R^{15}$ as listed in Table (II-1).

TABLE (II-16)

Table (II-16) contains the compounds of the general formula (II) in which
$R^{14}=CN$ and
$R^{15}$=as listed in Table (II-1).

TABLE (II-17)

Table (II-17) contains the compounds of the general formula (II) in which
$R^{14}=\text{—}OCH_2CF_3$ and
$R^{15}$=as listed in Table (II-1).

TABLE (II-18)

Table (II-18) contains the compounds of the general formula (II) in which
$R^{14}=\text{—}OCHF_2$ and
$R^{15}$=as listed in Table (II-1).

TABLE (II-19)

Table (II-19) contains the compounds of the general formula (II) in which
$R^{14}=Br$ and
$R^{15}$=as listed in Table (II-1).

TABLE (II-20)

Table (II-20) contains the compounds of the general formula (II) in which

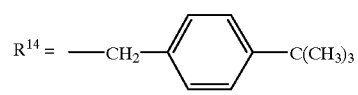

$R^{15}$=as listed in Table (II-1).

TABLE (II-21)

Table (II-21) contains the compounds of the general formula (II) in which
$R^{14}=Cl$ and
$R^{15}$=as listed in Table (II-1).

TABLE (II-22)

Table (II-22) contains the compounds of the general formula (II) in which
$R^{14}=OCH_3$ and
$R^{15}$=as listed in Table (II-1).

TABLE (II-23)

Table (II-23) contains the compounds of the general formula (II) in which
$R^{14}=\text{—}OC_2H_5$ and
$R^{15}$=as listed in Table (II-1).

TABLE (II-24)

Table (II-24) contains the compounds of the general formula (II) in which
$R^{14}=\text{—}OC_2H_7\text{-}i$ and
$R^{15}$=as listed in Table (II-1).

TABLE (II-25)

Table (II-25) contains the compounds of the general formula (II) in which
$R^{14}=\text{—}SCH_3$ and
$R^{15}$=as listed in Table (II-1).

TABLE (II-26)

Table (II-26) contains the compounds of the general formula (II) in which
$R^{14}=\text{—}SO_2CH_3$ and
$R^{15}$=as listed in Table (II-1).

TABLE (II-27)

Table (II-27) contains the compounds of the general formula (II) in which
$R^{14}=\text{—}SO_2C_2H_5$ and
$R^{15}$=as listed in Table (II-1).

TABLE (II-28)

Table (II-28) contains the compounds of the general formula (II) in which
$R^{14}=\text{—}SC_2H_5$ and
$R^{15}$=as listed in Table (II-1).

TABLE (II-29)

Table (II-29) contains the compounds of the general formula (II) in which
$R^{14}=\text{—}SC_3H_7\text{-}i$ and
$R^{15}$=as listed in Table (II-1).

TABLE (II-30)

TABLE (II-30) contains the compounds of the general formula (II) in which
$R^{14}=\text{—}SCHF_2$ and
$R^{15}$=as listed in Table (II-1).

TABLE (II-31)

Table (II-31) contains the compounds of the general formula (II) in which $R^{14}$=—$SCH_2CH_2CH_2F$ and
$R^{15}$=as listed in Table (II-1).

TABLE (II-32)

Table (II-32) contains the compounds of the general formula (II) in which
$R^{14}$=—$OCH_2CH_2CH_2F$ and
$R^{15}$=as listed in Table (II-1).

TABLE (II-33)

Table (II-33) contains the compounds of the general formula (II) in which

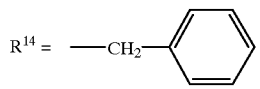

and
$R^{15}$=as listed in Table (II-1).

TABLE (II-34)

Table (II-34) contains the compounds of the general formula (II) in which
$R^{14}$=$CH_2CF_3$ and
$R^{15}$=as listed in Table (II-1).

TABLE (II-35)

Table (II-35) contains the compounds of the general formula (II) in which

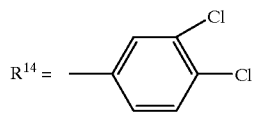

and
$R^{15}$=as listed in Table (II-1).

TABLE (II-36)

Table (II-36) contains the compounds of the general formula (II) in which

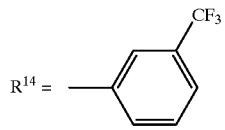

and
$R^{15}$=as listed in Table (II-1).

TABLE (II-37)

Table (II-37) contains the compounds of the general formula (II) in which
$R^{14}$=—$OCH_2CCl_3$ and
$R^{15}$=as listed in Table (II-1).

TABLE (II-38)

Table (II-38) contains the compounds of the general formula (II) in which
$R^{14}$=—$SCH_2Cl$ and
$R^{15}$=as listed in Table (II-1).

TABLE (II-39)

Table (II-39) contains the compounds of the general formula (II) in which
$R^{14}$=—$SCH_2F$ and
$R^{15}$=as listed in Table (II-1).

TABLE (II-40)

Table (II-40) contains the compounds of the general formula (II) in which
$R^{14}$=—$SCH_2CH_2F$ and
$R^{15}$=as listed in Table (II-1).

TABLE (II-41)

Table (II-41) contains the compounds of the general formula (II) in which
$R^{14}$=—$SCH_2CHF_2$ and
$R^{15}$=as listed in Table (II-1).

TABLE (II42)

Table (II-42) contains the compounds of the general formula (II) in which
$R^{14}$=—$SCH_2CF_3$ and
$R^{15}$=as listed in Table (II-1).

TABLE (II-43)

Table (II-43) contains the compounds of the general formula (II) in which
$R^{14}$=—$SCH_2CH_2CF_3$ and
$R^{15}$=as listed in Table (II-1).

TABLE (II-44)

Table (II-44) contains the compounds of the general formula (II) in which
$R^{14}$=—$SCH_2CH$=$CH_2$ and
$R^{15}$=as listed in Table (II-1).

TABLE (II-45)

Table (II-45) contains the compounds of the general formula (II) in which
$R^{14}$=—$SCH_2C$≡$CH$ and
$R^{15}$=as listed in Table (II-1).

TABLE (II-46)

Table (II-46) contains the compounds of the general formula (II) in which
$R^{14}$=—$SCH$=$C$=$CH_2$ and
$R^{15}$=as listed in Table (II-1).

TABLE (II-47)

Table (II-47) contains the compounds of the general formula (II) in which
$R^{14}$=—$OCH_2CF_2CHF_2$ and
$R^{15}$=as listed in Table (II-1).

TABLE (II-48)

Table (II-48) contains the compounds of the general formula (II) in which

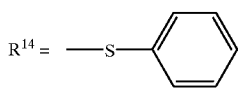

and $R^{15}$=as listed in Table (II-1).

TABLE (II-49)

Table (II-49) contains the compounds of the general formula (II) in which

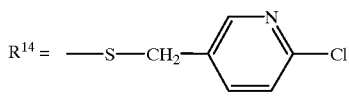

and $R^{15}$=as listed in Table (II-1).

Formula (III) provides a general definition of the halogen derivatives further required as starting materials for carrying out the process (a) according to the invention. In this formula (III), $R^{11}$, $R^{12}$, $R^{13}$ and $A^1$ each preferably and in particular represent those radicals which have already been mentioned in connection with the description of the compounds of the formula (Ia) according to the invention as preferred and particularly preferred for these substituents. Hal preferably represents fluorine, chlorine or bromine, in particular fluorine or chlorine.

The halogen derivatives of the formula (III) are generally known compounds of organic chemistry or obtainable in a generally known manner.

Formula (IV) provides a general definition of the hydrazine derivatives required as starting materials for carrying out the process (b) according to the invention. In this formula (IV), $R^{11}$, $R^{12}$, $R^{13}$ and $A^1$ each preferably and in particular represent those radicals which have already been mentioned in connection with the description of the compounds of the formula (Ia) according to the invention as preferred or particularly preferred for these substituents.

The hydrazine derivatives of the formula (IV) are known (cf. for example U.S. Pat. Nos. 4,127,575; 3,609,158; DE-A-25 58 399; J. Chem. Soc. C; 1971, 167–174) or can be obtained in a simple manner by known processes (cf. for example Houben-Weyl "Methoden der organischen Chemie" Volume X/2, p. 203, Thieme Verlag, Stuttgart, 1967).

Formula (V) provides a general definition of the iminocarboxylic esters further required as starting materials for carrying out the process (b) according to the invention. In this formula (V), $R^{21}$ and $R^{22}$ independently of one another each preferably represent $C_1$–$C_4$-alkyl, in particular methyl or ethyl. $R^{14-1}$ preferably or in particular has those meanings already mentioned above under $R^{14}$ in connection with the description of the compounds of the formula (Ia) according to the invention as preferred or particularly preferred for the corresponding substituents.

The aminocarboxylic esters of the formula (V) are known or obtainable by known processes (cf. for example Ber. 119, 2444–2457 [1986]; Bull. chem. Soc. Jpn. 55, 3943–3944 [1982]; Chem. Lett. 1982, 1015–1016; Chem. Lett. 1987, 1403–1404; J. Amer. chem. Soc. 95, 3957–3963 [1973]; J. org. Chem. 36, 3251–3252 [1971]).

The N-aryl-1,2,4-triazolin-5-ones of the formula (Id) required as starting materials for carrying out the process (c) according to the invention are compounds according to the invention.

Formula (VI) provides a general definition of the alkylating agents further required as starting materials for carrying out the process (c) according to the invention. In this formula (VI), $R^{15-1}$ preferably or in particular has the meanings already mentioned above under $R^{15}$ in connection with the description of the compounds of the formula (Ia) according to the invention as preferred or particularly preferred for the corresponding substituents. E represents a customary electron-withdrawing leaving radical, for example halogen, in particular chlorine, bromine or iodine; or represents respectively optionally substituted alkylsulphonyloxy, alkoxysulphonyloxy or arylsulphonyloxy, in particular methanesulphonyloxy, trifluoromethanesulphonyloxy, methoxysulphonyloxy, ethoxysulphonyloxy or p-toluenesulphonyloxy.

The alkylating agents of the formula (VI) are generally known compounds of organic chemistry.

Suitable diluents for carrying out the process (a) according to the invention are inert organic solvents. These include in particular aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform or carbon tetrachloride; ethers, such as diethyl ether, diisopropyl ether, dioxan, tetrahydrofuran or ethylene glycol dimethyl ether or ethylene glycol diethyl ether; ketones, such as acetone, butanone or methyl isobutyl ketone; nitriles, such as acetonitrile, propionitrile or benzonitrile; amides such as N,N-dimethylformamide, N,N-dimethylacetamide, N-methylformanilide, N-methylpyrrolidone or hexamethylphosphoric triamide or esters, such as methyl acetate or ethyl acetate.

The process (a) according to the invention is preferably carried out in the presence of a suitable reaction auxiliary. Suitable reaction auxiliaries are all customary inorganic or organic bases. These include for example alkaline earth metal or alkali metal hydroxides, such as sodium hydroxide, calcium hydroxide or potassium hydroxide, ammonium hydroxide, alkali metal carbonates, such as sodium carbonate, potassium carbonate, potassium bicarbonate or sodium bicarbonate, ammonium carbonate, alkali metal or alkaline earth metal acetates, such as sodium acetate, potassium acetate, calcium acetate or ammonium acetate, and tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU) and also piperidine.

When carrying out process (a) according to the invention, the reaction temperatures can be varied within a relatively wide range. In general, the reaction is carried out at temperatures between 0° C. and +180° C., preferably at temperatures between +20° C. and +120° C.

The process (a) according to the invention is generally carried out under atmospheric pressure. However, it is also possible to work under elevated or reduced pressure.

When carrying out process (a) according to the invention, generally 1.0 to 3.0 mol, preferably 1.0 to 1.5 mol, of halogen derivative of the formula (III) and, if appropriate, 1.0 to 3.0 mol, preferably 1.0 to 1.5 mol, of base (as reaction auxiliary) are employed per mole of 1H-triazolinone of the formula (II).

The reaction, the work-up and the isolation of the reaction products are carried out by conventional known processes (see also the Preparation Examples).

Suitable diluents for carrying out the process (b) according to the invention are inert organic solvents. Preference is given to using the solvents listed in the description of the practice of the process (a) according to the invention.

When carrying out process (b) according to the invention, the reaction temperatures can be varied within a relatively wide range. In general, the reaction is carried out at temperatures between −20° C. and +150° C., preferably at temperatures between 0° C. and +120° C.

The process (b) according to the invention is generally carried out under atmospheric pressure. However, it is also possible to work under elevated or reduced pressure.

When carrying out process (b) according to the invention, generally 1.0 to 3.0 mol, preferably 1.0 to 1.5 mol, of aminocarboxylic ester of the formula (V) are employed per mole of hydrazine derivative of the formula (IV).

The reaction, the work-up and the isolation of the reaction products are carried out by conventional known processes.

Suitable diluents for carrying out the process (c) according to the invention are inert organic solvents. These include in particular aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxan, tetrahydrofuran or ethylene glycol dimethyl ether or ethylene glycol diethyl ether; nitriles, such as acetonitrile, propionitrile or benzonitrile; amides such as N,N-dimethylformamide, N,N-dimethylacetamide, N-methylformanilide, N-methylpyrrolidone or hexamethylphosphoric triamide; esters, such as methyl acetate or ethyl acetate or sulphoxides, such as dimethyl sulphoxide.

If appropriate, the process (c) according to the invention can also be carried out in a two-phase system such as, for example. water/toluene or water/dichloromethane, if appropriate in the presence of a suitable phase transfer catalyst. Examples of such catalysts include: tetrabutylammonium iodide, tetrabutylammonium bromide, tetrabutylammonium chloride, tributyl-methylphosphonium bromide, trimethyl-$C_{13}$/$C_{15}$-alkylammonium chloride, trimethyl-$C_{13}$/$C_{15}$-alkylammonium bromide, dibenzyldimethyl-ammonium methylsulphate, dimethyl-$C_{12}$/$C_{14}$-alkyl-benzylammonium chloride, dimethyl-$C_{12}$/$C_{14}$-alkyl-benzylammonium bromide, tetrabutylammonium hydroxide, triethylbenzylammonium chloride, methyltrioctylammonium chloride, trimethylbenzylammonium chloride, 15-krone-5, 18-krone-6 or tris-[2(2-methoxyethoxy)-ethyl]-amine.

Process (c) according to the invention is preferably carried out in the presence of a suitable reaction auxiliary. Suitable reaction auxiliaries are all customary inorganic or organic bases. These include, for example, alkaline earth metal or alkali metal hydrides, hydroxides, amides, alkoxides, acetates, carbonates or bicarbonates, for example sodium hydride, sodium amide, sodium methoxide, sodium ethoxide, potassium tert-butoxide, sodium hydroxide, potassium hydroxide, sodium acetate, potassium acetate, calcium acetate, sodium carbonate, potassium carbonate, potassium bicarbonate or sodium bicarbonate, ammonium hydroxide, ammonium acetate, or ammonium carbonate and tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU).

When carrying out process (c) according to the invention, the reaction temperatures can be varied within a relatively wide range. In general, the reaction is carried out at temperatures between −20° C. and +150° C., preferably at temperatures between 0° C. and 120° C.

Process (c) according to the invention is generally carried out under atmospheric pressure. However, it is also possible to work under elevated or reduced pressure.

When carrying out process (c) according to the invention, generally 1.0 to 3.0 mol, preferably 1.0 to 2.0 mol, of alkylating agents of the formula (VI) and, if appropriate 1.0 to 3.0 mol, preferably 1.0 to 2.0 mol, of base (as reaction auxiliary) are employed per mole of N-aryl-1,2,4-triazolin-5-one of the formula (Id).

The reaction, the work-up and the isolation of the reaction products are carried out by conventional known processes.

The active compounds of the formula (I) which are usable according to the invention, having good crop tolerance and favourable homeotherm safety, are suitable for controlling animal pests, in particular insects, arachnida and nematodes, which are encountered in agriculture, in forestry, in the protection of stored products and of materials, and in the hygiene field. They can preferably be used as crop protection agents. They are active against normally sensitive and resistant species and against all or some stages of development. The abovementioned pests include:

From the order of Isopoda, for example, *Oniscus asellus, Armadillidium vulgare* and *Porcellio scaber.*

From the order of the Diplopoda, for example, *Blaniulus guttulatus.* From the order of the Chilopoda, for example, *Geophilus carpophagus* and *Scutigera spec.* From the order of the Symphyla, for example, *Scutigerella immaculata.* From the order of the Thysanura, for example, *Lepisma saccharina.* From the order of the Collembola, for example, *Onychiurus armatus.*

From the order of the Orthoptera, for example, *Blatta orientalis, Periplaneta americana, Leucophaea maderae, Blatella germanica, Acheta domesticus,* Gryllotalpa spp., *Locusta migratoria migratorioides, Melanoplus differentialis, Schistocerca gregaria* and Supella spp.

From the order of the Dermaptera, for example, *Forficula auricularia.* From the order of the Isoptera, for example, Reticulitermes spp.

From the order of the Anoplura, for example, *Phylloxera vastatrix,* Pemphigus spp., Phthirus spp., Pediculus spp., Haematopinus spp., Linognathus spp. and Solenopotes spp. From the order of the Mallophaga, for example, Trichodectes spp., Damalinea spp., Trimenopon spp., Monopon spp., Trioton spp., Bovicola spp., Werneckiella spp., Lepikentron spp. and Felicola spp. From the order of the Thysanoptera, for example, *Hercinothrips femoralis* and *Thrips tabaci.* From the order of the Heteroptera, for example, Eurygaster spp., *Dysdercus intermedius, Piesma quadrata,* Cimex spp., Rhodnius spp., Triatoma spp. and Panstrongylus spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp, *Bucculatrix thurberiella, Phyllocnistis citrella,* Agrotis spp., Euxoa spp., Feltia spp., *Earias insulana,* Heliothis spp., *Spodoptera exigua,*

*Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Hylotrupes bajulus, Agelastica alni, Leptinotarsa decemlineata, Phaedon cochleariae,* Diabrotica spp., *Psylliodes chrysocephala, Epilachna varive stis,* Atomaria spp., *Oryzaephilus surinamensis, Antho nomus* spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., *Cono derus* spp., *Melolontha melolontha, Amphimallon solsti tialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Lucilia spp., Chrysomyia spp., Cuterebra spp., Tannia spp., *Bibio hortulanus, Oscinella frit,* Phorbia spp., *Pegomyia hyoscyami, Ceratitis capitata, Dacus oleae, Tipula paludosa,* Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Hydrotaea spp., Stomoxys spp., Haematobia spp., Morellia spp., Fannia spp., Glossina spp., Calliphora spp., Wohlfahrtia spp., Sarcophaga spp., Oestrus spp., Hypoderma spp., Gasterophilus spp., Hippobosca spp., Lipoptena spp., Melophagus spp., Muscina spp.

From the order of the Siphonapterida, for example, Xenopsylla spp., Ceratophyllus spp., Pulex spp. and Ctenocephalides spp. From the order of the Arachnida, for example, *Scorpio maurus* and *Latrodectus mactans.*

From the order of the Acarina, for example, Myocoptes spp., Acarus siro, Argas spp:, Omithodoros spp., Ornithonyssus spp., Dermanyssus spp., *Eriophyes ribis, Phyllocoptruta oleivora,* Boophilus spp., Rhipicephalus spp., Amblyomma spp., Hyalomma spp., Ixodes spp., Tarsonemus spp., *Bryobia praetiosa,* Panonychus spp., Tetranychus spp., Dermacentor spp., Haemaphysalis spp., Raillietia spp., Pneumonyssus spp., Sternostorma spp., Varroa spp. and Otobius spp.

From the order of Actinedida (Prostigmata) and Acaridida (Astigmata), for example: Acarapis spp., Cheyletiella spp., Ornithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres spp., Knemidocoptes spp., Cytodites spp. and Laminosioptes spp.

The plant-parasitic nematodes include, for example, Pratylenchus spp., *Radopholus similis, Ditylenchus dipsaci, Tylenchulus semipenetrans,* Heterodera spp., Globodera spp., Meloidogyne spp., Aphelenchoides spp., Longidorus spp., Xiphinema spp. and Trichodorus spp.

The active compounds according to the invention have a high insecticidal activity.

They can be used to particularly good effect for controlling leaf and soil-dwelling insects which are injurious to plants, such as, for example, against the larvae of the mustard beetle (*Phaedon cochleariae*), against the larvae of the green rice leaf hopper (*Nephotettix cincticeps*) or against the caterpillars of the cabbage moth (*Plutella maculipennis*), furthermore against the caterpillars of the owlet moth (*Spodoptera frugiperda*) and against the tobacco bud worm (*Heliothis virescens*).

Additionally, the active compounds of the formula (I) which can be used according to the invention also have an acaricidal and fungicidal activity, for example against *Pyricularia oryzae* in rice.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents, for example, can also be used as auxiliary solvents. Suitable liquid solvents are in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

Suitable solid carriers are:

for example ammonium salts and ground natural minerals, such as kaolins, clays, talc, chalk, quartz, attapulgite, montmorillonite or diatomaceous earth, and ground synthetic minerals, such as finely divided silica, alumina and silicates, suitable solid carriers for granules are: for example crushed and fractionated natural rocks such as calcite, marble, pumice, sepiolite and dolomite as well as synthetic granules of inorganic and organic meals, and granules of organic material such as sawdust, coconut shells, maize cobs and tobacco stalks; suitable emulsifying and/or foam-forming agents are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as protein hydrolysates; dispersing agents suitable are: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general comprise between 0.1 and 95 per cent by weight of active compound, preferably between 0.5 and 90%.

The active compound according to the invention can be present in its commercially available formulations and in the use forms prepared from these formulations, as a mixture with other active compounds, such as insecticides, attractants, sterilizing agents, bactericides, acaricides, nematicides, fungicides, growth-regulating substances or herbicides. The insecticides include, for example, phosphates, carbamates, carboxylates, chlorinated hydrocarbons, phenylureas, substances produced by microorganisms, etc.

Examples of particularly advantageous mixture components are the following compounds:

Fungicides 2-aminobutane; 2-anilino-4-methyl-6-cyclopropyl-pyrimidine; 2',6'-dibromo-2-methyl-4'-trifluoromethoxy-4'-trifluoro-methyl-1,3-thiazole-5-carboxanilide; 2,6-dichloro-N-(4-trifluoromethylbenzyl)-benzamide; (E)2-methoxyimino-N-methyl-2-(2-phenoxyphenyl)-acetamide; 8-hydroxyquinoline sulphate; methyl (E)-2-{2-[6-(2-cyanophenoxy)-pyrimidin-4-yloxy]-phenyl}-3-methoxyacrylate; methyl (E)-methoximino-[alpha-(o-tolyloxy)-o-tolyl]-acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulphamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulphocarb, methfuroxam, metiram, metsulphovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamate, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebucanozole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole, validamycin A, vinclozolin, zineb, ziram.

Bactericides

Bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides

Abamectin, AC 303 630, acephate, acrinathrin, alanycarb, aldicarb, alphamethrin, amitraz, avermectin, AZ 60541, azadirachtin, azinphos A, azinphos M, azocyclotin,

*Bacillus thuringiensis*, bendiocarb, benfuracarb, bensultap, beta-cyluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, CGA 157 419, CGA 184699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mervinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyradaphenthion, pyresmethrin, pyrethrum, pyridaben, pyrimidifen, pyriproxifen, quinalphos,

RH 5992, salithion, sebufos, silafluofen, sulfotep, sulprofos, tebufenozid, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, YI 5301/5302, zetamethrin.

Herbicides

For example anilides such as, for example, diflufenican and propanil; arylcarboxylic acids such as, for example, dichloropicolinic acid, dicamba and picloram; aryloxyalkanoic acids such as, for example, 2,4-D, 2,4-DB, 2,4-DP, fluroxypyr, MCPA, MCPP and triclopyr; aryloxy-phenoxyalkanoic esters such as, for example, diclofopmethyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenz-thiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulphonylureas such as, for example, amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribenuron-methyl; thiocarbamates such as, for example, butylate, cycloate, diallate, EPTC, esprocarb, molinate, prosulfocarb, thiobencarb and triallate; triazines such as, for example, atrazine, cyanazine, simazine, simetryne, terbutryne and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

The active compound according to the invention can furthermore be present in its commercially available formulations and in the use forms prepared from these formulations, as a mixture with synergistic agents. Synergistic agents are compounds which increase the action of the active compounds without it being necessary for the synergistic agent added to be active itself.

The active compound content of the use forms prepared from the commercially available formulations can vary within wide ranges. The active compound concentration of the use forms can be from 0.0000001 to 95% by weight of active compound, preferably between 0.0001 and 1% by weight.

The compounds are employed in a customary manner appropriate for the use forms.

When used against hygiene and stored products pests, the active compound is distinguished by an excellent residual action on wood and clay as well as a good stability to alkali on limed substrates.

The active compounds according to the invention are not only active against plant, hygiene and stored-product pests, but also, in the veterinary medicine sector, against animal parasites (ectoparasites), such as ixodid ticks, argasid ticks, scab mites, trombiculid mites, flies (stinging and sucking), parasitic fly larvae, lice, hair lice, bird lice and fleas. For example, they show an outstanding activity against ticks such as, for example, *Boophilus microplus.*

The active compounds of the formula (I) according to the invention are also suitable for controlling arthropods which attack agricultural livestock, such as, for example, cattle, sheep, goats, horses, pigs, donkeys, camels, buffalo, rabbits, chickens, turkeys, ducks, geese, honey bees, other domestic animals, such as, for example, dogs, cats, cage birds, aquarium fish, and so-called experimental animals such as, for example, hamsters, guinea-pigs, rats and mice. By controlling these arthropods, it is intended to reduce mortality and decreased performance (in meat, milk, wool, hides, eggs, honey etc.), so that more economical and simpler animal keeping is made possible by using the active compounds according to the invention.

In the veterinary sector, the active compounds according to the invention are used in a known manner by enteral administration, for example in the form of tablets, capsules, drinks, drenches, granules, pastes, boluscs, the feed-through method, suppositories, by parenteral administration, such as, for example, by means of injections (intramuscular, subcutaneous, intravenous, intraperitoneal and the like), implants, by nasal application, by dermal administration, for example in the form of dipping or bathing, spraying, pouring-on and spotting-on, washing, dusting, and with the aid of shaped articles which comprise active compound, such as collars, ear tags, tail marks, limb bands, halters, marking devices etc.

When administered to livestock, poultry, domestic animals etc., the active compounds of the formula (I) can be used as formulations (for example powders, emulsions, flowables) which comprise the active compounds in an amount of 1 to 80% by weight, either directly or after dilution by a factor of 100 to 10,000, or they may be used in the form of a chemical bath.

Furthermore, it has been found that the compounds of the formula (I) according to the invention have a potent insecticidal action against insects which destroy industrial materials.

The following insects may be mentioned by way of example and as being preferred, but without any limitation:

Beetles, such as

*Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis,* Zyleborus spec., Tryptodendron spec., *Apate monachus, Bostrychus capucins, Heterobostrychus brunneus,* Sinoxylon spec., *Dinoderus minutus.*

Dermapterans, such as

*Sirex juvencus, Urocerus gigas, Urocerus gigas taignus, Urocerus augur.*

Termites, such as

Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.

Bristletails, such as *Lepisma saccharina.*

Industrial materials are to be understood as meaning, in the present context, non-living materials such as, preferably, synthetic materials, glues, sizes, paper and board, leather, wood and timber products, and paint.

The materials to be protected very particularly against attack by insects are wood and timber products.

Wood and timber products which can be protected by the composition according to the invention or mixtures comprising such a composition are to be understood as meaning, for example, construction timber, wooden beams, railway sleepers, bridge components, jetties, wooden vehicles, boxes, pallets, containers, telephone poles, wood lagging, windows and doors made of wood, plywood, particle board, joiner's articles, or wood products which, quite generally, are used in the construction of houses or in joinery.

The active compounds can be used as such, in the form of concentrates or generally customary formulations, such as powders, granules, solutions, suspensions, emulsions or pastes.

The formulations mentioned can be prepared in a manner known per se, for example by mixing the active compounds with at least one solvent or diluent, emulsifier, dispersant and/or binder or fixative, water repellent, if appropriate desiccants and UV stabilizers and, if appropriate, colorants and pigments and other processing auxiliaries.

The insecticidal compositions or concentrates used for the protection of wood and wooden materials comprise the active compound according to the invention at a concentration of 0.0001 to 95% by weight, in particular 0.001 to 60% by weight.

The amount of the compositions or concentrates employed depends on the species and the occurrence of the insects and on the medium. The optimum rate of application can be determined upon use in each case by test series. However, in general, it suffices to employ 0.0001 to 20% by weight, preferably 0.001 to 10% by weight, of the active compound, based on the material to be protected.

The solvent and/or diluent used is an organochemical solvent or solvent mixture and/or an oily or oil-type organochemical solvent or solvent mixture of low volatility and/or a polar organochemical solvent or solvent mixture and/or water and, if appropriate, an emulsifier and/or wetting agent.

Organochemical solvents which are preferably employed are oily or oil-type solvents having an evaporation number of above 35 and a flashpoint of above 30° C., preferably above 45° C. Substances which are used as such oily and oil-type solvents which have low volatility and are insoluble in water are suitable mineral oils or their aromatic fractions, or mineral-oil-containing solvent mixtures, preferably white spirit, petroleum and/or alkylbenzene.

Substances which are advantageously used are mineral oils with a boiling range of 170 to 220° C., white spirit with a boiling range of 170 to 220° C., spindle oil with a boiling range of 250 to 350° C., petroleum or aromatics of boiling range 160 to 280° C., essence of turpentine and the like.

In a preferred embodiment, liquid aliphatic hydrocarbons with a boiling range of 180 v to 210° C. or high-boiling mixtures of aromatic and aliphatic hydrocarbons with a boiling range of 180 to 220° C. and/or spindle oil and/or monochloronaphthalene, preferably -monochloronaphthalene, are used.

The organic oily or oil-type solvents of low volatility having an evaporation number of above 35 and a flashpoint of above 30° C., preferably above 45° C., can be partially replaced by organochemical solvents of high or medium volatility, with the proviso that the solvent mixture likewise has an evaporation number of above 35 and a flashpoint of above 30° C., preferably above 45° C., and that the insecticide/fungicide mixture is soluble or emulsifiable in this solvent mixture.

In a preferred embodiment, part of the organochemical solvent or solvent mixture is replaced by an aliphatic polar organochemical solvent or solvent mixture. Substances which are preferably used are aliphatic organochemical solvents having hydroxyl and/or ester and/or ether groups, such as, for example, glycol ether, esters and the like.

The organochemical binders used within the scope of the present invention are the synthetic resins and/or binding drying oils which are known per se and can be diluted with water and/or are soluble or dispersible or emulsifiable in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin, such as indene/coumarone resin, silicone resin, drying vegetable and/or drying oils and/or physically drying binders based on a natural and/or synthetic resin.

The synthetic resin used as the binder can be employed in the form of an emulsion, dispersion or solution. Up to 10% by weight of bitumen or bituminous substances can also be used as binders. In addition, colorants, pigments, water repellents, odour-masking substances and inhibitors or anti-corrosives known per se and the like can be employed.

The composition or the concentrate preferably comprises, in accordance with the invention, at least one alkyd resin or modified alkyd resin and/or a drying vegetable oil as the organochemical binder. Preferably used according to the invention are alkyd resins with an oil content of over 45% by weight, preferably 50 to 68% by weight.

All or some of the abovementioned binder can be replaced by a fixative (mixture) or a plasticizer (mixture). These additives are intended to prevent volatilization of the active compounds and crystallization or precipitation. They preferably replace 0.01 to 30% of the binder (based on 100% of binder employed).

The plasticizers are from the chemical classes of phthalic esters, such as dibutyl phthalate, dioctyl phthalate or benzylbutyl phthalate, phosphoric esters, such as tributyl phosphate, adipic esters, such as di-(2-ethylhexyl) adipate, stearates, such as butyl stearate or amyl stearate, oleates, such as butyl oleate, glycerol ethers or relatively high-molecular-weight glycol ethers, glycerol esters and p-toluene-sulphonic esters.

Fixatives are chemically based on polyvinyl alkyl ethers, such as, for example, polyvinyl methyl ether, or ketones, such as benzophenone or ethylene benzophenone.

Particularly suitable as a solvent or diluent is also water, if appropriate as a mixture with one or more of the abovementioned organochemical solvents or diluents, emulsifiers and dispersants.

Particularly effective protection of wood is achieved by large-scale industrial impregnation processes, for example vacuum, double-vacuum or pressure processes.

If appropriate, the ready-to-use compositions can additionally comprise other insecticides and, if appropriate, additionally one or more fungicides.

Suitable additional components which may be admixed are, preferably, the insecticides and fungicides mentioned in WO 94/29 268. The compounds mentioned in that document are expressly part of the present application.

Very particularly preferred components which may be admixed are insecticides, such as chlorpyriphos, phoxim, silafluofm, alphamethrin, cyfluthrin, cypermethrin, deltamethrin, permethrin, imidacloprid, NI-25, flufenoxuron, hexaflumuron and triflumuron, and fungicides, such as epoxyconazole, hexaconazole, azaconazole, propiconazole, tebuconazole, cyproconazole, metconazole, imazalil, dichlorofluanid, tolylfluanid, 3-iodo- 2-propinylbutyl carbamate, N-octyl-isothiazolin-3-one and 4,5-dichloro-N-octylisothiazolin-3-one.

The preparation and the use of the active compounds according to the invention can be seen from the examples below.

PREPARATION EXAMPLES

Example 1

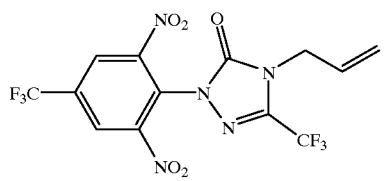

(Process a)

At room temperature, 3.86 g (0.02 mol) of 3-trifluoromethyl-4-propenyl-1H-1,2,4-triazolin-5-one and 2.76 g (0.02 mol) of potassium carbonate in 100 ml of dimethyl sulphoxide are admixed with 5.41 g (0.02 mol) of 2,6-dinitro-4-trifluoromethyl-chlorobenzene and stirred for 4 hours at 80° C. and for 1 hour at 120° C. For work-up, the reaction mixture is stirred with ice-water and the precipitated product is filtered off with suction and recrystallized from isopropanol.

4.4 g (52% of theory) of 1-(2,6-dinitro-4-trifluoromethyl-phenyl)-3-trifluoromethyl-4-propenyl-1,2,4-triazolin-5-one of melting point 136° C. are obtained.

By the method of Example 1 and according to the general description of the preparation processes according to the invention, the compounds of the formula (Ia) listed in Table 1 below can be prepared.

TABLE 1

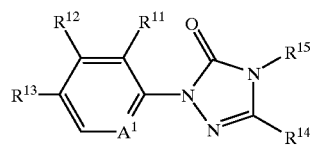

(Ia)

| Ex. No.: | $R^{11}$ | $R^{12}$ | $R^{13}$ | $A^1$ | $R^{14}$ | $R^{15}$ | Physical properties |
|---|---|---|---|---|---|---|---|
| 2 | $NO_2$ | H | $CF_3$ | $C-NO_2$ | $CH_3$ | $CH_3$ | mp.: 200–202° C. |
| 3 | Cl | F | $CF_3$ | C—Cl | $CH_3$ | $OCH_3$ | mp.: 65–67° C. |
| 4 | Cl | H | $CF_3$ | C—Cl | $CF_3$ | $C_2H_5$ | mp.: 117° C. |
| 5 | Cl | H | $CF_3$ | C—Cl | $CF_3$ | cyclopropyl | mp.: 102° C. |
| 6 | F | H | $CF_3$ | C—Cl | $CF_3$ | 2,2-dichlorocyclopropyl-methyl | $^1$H NMR (CDCl$_3$): δ = 3.80–3.95; 7.45–7.50; 7.65 ppm |
| 7 | Cl | H | $CF_3$ | C—Cl | $CF_3$ | 2,2-dichlorocyclopropyl-methyl | mp.: 69–70° C. |
| 8 | F | H | $CF_3$ | C—Cl | $CF_3$ | cyclopropyl | mp.: 110–111° C. |
| 9 | Cl | F | $CF_3$ | C—Cl | $CF_3$ | cyclopropyl | mp.: 103–104° C. |
| 10 | $NO_2$ | H | $CF_3$ | $C-NO_2$ | $CF_3$ | cyclopropyl | mp.: 140–141° C. |
| 11 | Cl | H | $CF_3$ | C—Cl | $CF_3$ | allyl | $^1$H NMR (CDCl$_3$): δ = 4.48–4.50; 5.90–6.00; 7.75 ppm |
| 12 | Cl | H | $CF_3$ | N | $CF_3$ | cyclopropyl | mp.: 77–79° C. |
| 13 | $CF_3$ | H | $CF_3$ | $C-CF_3$ | $CF_3$ | cyclopropyl | mp.: 80–81° C. |

TABLE 1-continued

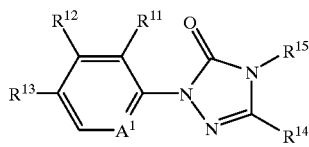

(Ia)

| Ex. No.: | $R^{11}$ | $R^{12}$ | $R^{13}$ | $A^1$ | $R^{14}$ | $R^{15}$ | Physical properties |
|---|---|---|---|---|---|---|---|
| 14 | Cl | H | $CF_3$ | C—Cl | $CF_2CF_3$ | $CH_3$ | mp.: 156–158° C. |
| 15 | Cl | H | $CF_3$ | C—Cl | $CHF_2$ | $C_2H_5$ | mp.: 114–116° C. |
| 16 | Cl | H | $CF_3$ | C—Cl | $CF_2CHF_2$ | $CH_3$ | mp.: 113–115° C. |
| 17 | Cl | H | $CF_3$ | C—Cl | $CH_3$ | $NH_2$ | mp.: 167° C. |
| 18 | Cl | H | $CF_3$ | C—Cl | $CH_3$ | $SO_2CF_2CH_3$ | mp.: 178–180° C. |
| 19 | Cl | H | $CF_3$ | C—Cl | $CH_3$ | $CH_3$ | mp.: 144–146° C. |
| 20 | Cl | H | $CF_3$ | C—Cl | cyclopropyl | $CH_3$ | mp.: 121–123° C. |
| 21 | Cl | H | $CF_3$ | C—CN | $CF_3$ | cyclopropyl | mp.: 105–107° C. |
| 22 | Cl | H | $CF_3$ | C—Cl | $CF_3$ | $CH_3$ | mp.: 136° C. |
| 23 | F | H | $CF_3$ | C—Cl | $CF_3$ | $CH_3$ | mp.: 78° C. |
| 24 | Cl | H | $CF_3$ | N | $CF_3$ | $CH_3$ | mp.: 56° C. |
| 25 | $NO_2$ | H | $CF_3$ | C—Cl | $CF_3$ | $CH_3$ | mp.: 100° C. |
| 26 | $NO_2$ | H | $CF_3$ | C—OH | $CF_3$ | $CH_3$ | $n_D^{20}$ = 1.4809 |
| 27 | Cl | H | $CF_3$ | C—Cl | $CF_3$ | $CH(CH_3)_2$ | mp.: 81° C. |
| 28 | F | H | $CF_3$ | C—Cl | $CF_3$ | $CH(CH_3)_2$ | mp.: 34° C. |
| 29 | $NO_2$ | H | $CF_3$ | C—$NO_2$ | $CF_3$ | $CH_3$ | mp.: 155° C. |
| 30 | Cl | H | $CF_3$ | C—Cl | $CF_3$ | $NH_2$ | mp.: 100° C. |
| 31 | Cl | H | $CF_3$ | C—Cl | $CF_3$ | H | mp.: 165° C. |
| 32 | Cl | H | $CF_3$ | C—CN | $CF_3$ | $CH_3$ | mp.: 110° C. |
| 33 | Cl | H | $CF_3$ | C—CN | $CF_3$ | $NH_2$ | mp.: 126° C. |
| 34 | Cl | H | $CF_3$ | C—Cl | $CH(CH_3)_2$ | $NH_2$ | mp.: 134° C. |
| 35 | Cl | H | $CF_3$ | C—Cl | benzyl | $NH_2$ | mp.: 191° C. |
| 36 | Cl | H | $CF_3$ | C—Cl | $C(CH_3)_3$ | $NH_2$ | mp.: 174° C. |
| 37 | Cl | H | $CF_3$ | C—Cl | cyclopropyl | $NH_2$ | mp.: 139° C. |
| 38 | Cl | H | $CF_3$ | C—Cl | $OCHF_2$ | $CH_3$ | mp.: 115° C. |
| 39 | Cl | H | $CF_3$ | C—Cl | $CH(CH_3)_2$ | H | mp.: 185° C. |
| 40 | Cl | H | $CF_3$ | C—Cl | benzyl | H | mp.: 188° C. |
| 41 | Cl | H | $CF_3$ | C—Cl | $CF_3$ | CN | mp.: 80° C. |
| 42 | Cl | H | $CF_3$ | C—Cl | $C(CH_3)_3$ | H | mp.: 209° C. |
| 43 | Cl | H | $CF_3$ | C—Cl | cyclopropyl | H | mp.: 191° C. |
| 44 | Cl | H | $CF_3$ | C—Cl | benzyl | CN | mp.: 76° C. |
| 45 | Cl | H | $CF_3$ | C—Cl | $C(CH_3)_3$ | CN | mp.: 155° C. |
| 46 | Cl | H | $CF_3$ | C—Cl | cyclopropyl | CN | mp.: 163° C. |

TABLE 1-continued (Ia)

structure: benzene ring with substituents $R^{12}$, $R^{11}$ (on adjacent positions), $R^{13}$, connected via $A^1$ to a triazolinone ring bearing $R^{15}$ (on N) and $R^{14}$.

| Ex. No.: | $R^{11}$ | $R^{12}$ | $R^{13}$ | $A^1$ | $R^{14}$ | $R^{15}$ | Physical properties |
|---|---|---|---|---|---|---|---|
| 47 | Cl | H | $CF_3$ | C—Cl | $CH(CH_3)_2$ | CN | mp.: 117° C. |
| 48 | Cl | H | $CF_3$ | C—Cl | $OCH_2CF_3$ | CH₂CH=CH₂ | mp.: 89° C. |
| 49 | Cl | H | $CF_3$ | C—Cl | $OCH_2CF_3$ | cyclopropyl | mp.: 73° C. |
| 50 | Cl | H | $CF_3$ | C—Cl | cyclopropyl | cyclopropyl | mp.: 93° C. |
| 51 | Cl | H | $CF_3$ | C—Cl | $SCH_2CF_3$ | cyclopropyl | $^1$H NMR(CDCl$_3$): δ = 1.1–1.2; 2.8; 3.82; 7.71 ppm |
| 52 | Cl | H | $CF_3$ | C—Cl | SPh | cyclopropyl | mp.: 139° C. |
| 53 | Cl | H | $CF_3$ | C—Cl | $SCH_3$ | cyclopropyl | mp.: 101° C. |
| 54 | Cl | H | $CF_3$ | C—Cl | $SO_2CH_3$ | $NH_2$ | mp.: 161° C. |
| 55 | Cl | H | $CF_3$ | C—Cl | $OCH_2CH_3$ | $NH_2$ | mp.: 130° C. |
| 56 | Cl | H | $CF_3$ | C—Cl | $OCH(CH_3)_2$ | $NH_2$ | mp.: 174° C. |
| 57 | Cl | H | $CF_3$ | C—Cl | $OCH_2CF_3$ | $NH_2$ | mp.: 132° C. |
| 58 | Cl | H | $CF_3$ | C—Cl | $OCH_2CH=CH_2$ | cyclopropyl | $^1$H NMR(CDCl$_3$): δ = 0.99–1.2; 2.79; 4.09–4.15; 7.68 ppm |
| 59 | Cl | H | $CF_3$ | C—Cl | $OCH_2CH_3$ | H | mp.: 159° C. |
| 60 | Cl | H | $CF_3$ | C—Cl | $OCH_2CH_3$ | CN | mp.: 137° C. |
| 61 | Cl | H | $CF_3$ | C—Cl | $OCH_2CF_3$ | H | mp.: 176° C. |
| 62 | Cl | H | $CF_3$ | C—Cl | $OCH_2CF_3$ | CN | mp.: 164° C. |
| 63 | Cl | H | $CF_3$ | C—Cl | $OCH(CH_3)_2$ | H | mp.: 192° C. |
| 64 | Cl | H | $CF_3$ | C—Cl | $OCH(CH_3)_2$ | CN | mp.: 125° C. |
| 65 | Cl | H | $CF_3$ | C—Cl | $SCH_3$ | H | mp.: 158–161° C. |
| 66 | Cl | H | $CF_3$ | C—Cl | $SCH_3$ | $CH_3$ | mp.: 112–115° C. |
| 67 | Cl | H | $CF_3$ | C—Cl | $SCHF_2$ | H | mp.: 188–192° C. |
| 68 | Cl | H | $CF_3$ | C—Cl | $SCHF_2$ | $CHF_2$ | $^1$H NMR(CDCl$_3$) δ = 7.78 ppm |
| 69 | Cl | H | $CF_3$ | C—Cl | $SCH_3$ | $CHF_2$ | mp.: 103–105° C. |
| 70 | F | H | $CF_3$ | C—Cl | Br | $CH_3$ | mp.: 113–115° C. |
| 71 | F | H | $CF_3$ | C—Cl | $CH_3$ | $OCH_3$ | mp.: 64–66° C. |
| 72 | F | H | $CF_3$ | C—Cl | $CH_3$ | —N=C(CH$_3$)CH$_2$—C$_3$H$_7$i | $^1$H NMR(CDCl$_3$) δ = 7.44 ppm |
| 73 | F | H | $CF_3$ | C—Cl | $CH_3$ | $NH_2$ | mp.: 104° C. |
| 74 | F | H | $CF_3$ | C—Cl | $OCH_3$ | $CH_3$ | mp.: 113–115° C. |
| 75 | Cl | H | $CF_3$ | C—Cl | Br | $CH_3$ | mp.: 143° C. |
| 76 | Cl | H | $CF_3$ | C—Cl | $CH_3$ | $OCH_3$ | mp.: 98° C. |
| 77 | F | H | $CF_3$ | C—Cl | Ph | $CH_3$ | mp.: 115° C. |

TABLE 1-continued

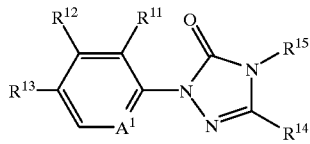

(Ia)

| Ex. No.: | $R^{11}$ | $R^{12}$ | $R^{13}$ | $A^1$ | $R^{14}$ | $R^{15}$ | Physical properties |
|---|---|---|---|---|---|---|---|
| 78 | Cl | H | $CF_3$ | C—Cl | $OCH(CH_3)_2$ | $CH_3$ | mp.: 93° C. |
| 79 | Cl | H | $CF_3$ | C—Cl | CN | $CH_3$ | mp.: 178° C. |
| 80 | Cl | H | $CF_3$ | C—Cl | $CH_3$ | CN | mp.: 128° C. |
| 81 | Cl | H | $CF_3$ | C—Cl | $CH_3$ | $SCFCl_2$ | mp.: 89° C. |
| 82 | Cl | H | $CF_3$ | C—Cl | —C$_6$H$_5$ | $CH_3$ | mp.: 138° C. |
| 83 | Cl | H | $CF_3$ | C—Cl | —C$_6$H$_3$Cl$_2$ | $CH_3$ | mp.: 78° C. |
| 84 | Cl | H | $CF_3$ | C—Cl | $CH(CH_3)C_2H_5$ | H | mp.: 159° C. |
| 85 | Cl | H | $CF_3$ | C—Cl | —C$_6$H$_5$ | H | mp.: >260° C. |
| 86 | Cl | H | $CF_3$ | C—Cl | $CH(CH_3)C_2H_5$ | $SCFCl_2$ | $^1$H NMR(CDCl$_3$) δ = 7.72 ppm |
| 87 | Cl | H | $CF_3$ | C—Cl | $CH(CH_3)C_2H_5$ | CN | mp.: 42–43° C. |
| 88 | Cl | H | $CF_3$ | C—Cl | —C$_6$H$_5$ | CN | $^1$H NMR(CDCl$_3$) δ = 7.78 ppm |
| 89 | Cl | H | $CF_3$ | C—Cl | $CH(CH_3)C_2H_5$ | $SCF_3$ | $^1$H NMR(CDCl$_3$) δ = 7.72 ppm |
| 90 | Cl | H | $CF_3$ | C—Cl | $OCH_2CF_3$ | $CH_3$ | mp.: 158° C. |
| 91 | $OCH_2CF_3$ | H | $CF_3$ | C—Cl | $OCH_2CF_3$ | $CH_3$ | mp.: 109° C. |
| 92 | Cl | H | $CF_3$ | C—Cl | $CF_3$ | —C$_6$H$_5$ | mp.: 142° C. |
| 93 | Cl | H | $CF_3$ | C—CN | $CF_3$ | —C$_6$H$_5$ | mp.: 112° C. |
| 94 | Cl | H | $CF_3$ | C—CN | $CF_3$ | $C_3H_7$-i | mp.: 109° C. |
| 95 | Cl | H | $SO_2CF_3$ | C—Cl | $CF_3$ | cyclopropyl | mp.: 160–62° C. |
| 96 | Cl | H | $CF_3$ | C—H | $CF_3$ | cyclopropyl | mp.: 95–96° C. |
| 97 | Cl | H | $CF_3$ | C—Cl | $CF_3$ | cyclohexyl | $^1$H NMR(CDCl$_3$) δ = 1.90–1.95 ppm 3.90–4.00 ppm 7.75 ppm |

TABLE 1-continued

(Ia)

| Ex. No.: | R11 | R12 | R13 | A1 | R14 | R15 | Physical properties |
|---|---|---|---|---|---|---|---|
| 98 | Cl | H | CF3 | C—Cl | Br | cyclopropyl | mp.: 89° C. |
| 99 | Cl | H | CF3 | C—Cl | CF3 | cyclopentyl | mp.: 92° C. |
| 100 | Br | H | CF3 | C—Cl | CF3 | cyclopropyl | mp.: 87–88° C. |
| 101 | Cl | H | —SO2CF3 | C—Cl | Br | cyclopropyl | mp.: 88° C. |
| 102 | Cl | H | CF3 | C—Cl | Cl | cyclopropyl | mp.: 84° C. |
| 103 | Cl | H | CF3 | C—CN | Br | cyclopropyl | mp.: 118° C. |
| 104 | Cl | H | CF3 | C—Cl | CF3 | —(CH2)3OCH3 | 1H NMR (CDCl3): δ = 2.1–2.15; 3.5–3.55; 7.75 ppm |
| 105 | Cl | H | CF3 | C—Cl | CF3 | —CH2CF3 | mp.: 55–59° C. |
| 106 | Cl | H | CF3 | C—CN | CF3 | —CH2CF3 | mp.: 107–109° C. |
| 107 | Cl | H | CF3 | C—CN | CF3 | cyclohexyl | mp.: 83–85° C. |
| 108 | Cl | H | CF3 | C—Cl | —CH2O-phenyl | CH3 | mp.: 110° C. |
| 109 | Cl | H | —SO2CF3 | C—Cl | cyclopropyl | cyclopropyl | mp.: 145° C. |
| 110 | Cl | H | CF3 | C—Cl | C4H5-i | cyclopropyl | 1H NMR(DMSO): δ = 1.00; 2.16; 2.60; 2.94; 8.19 pm |
| 111 | Cl | H | CF3 | C—Cl | C4H5-s | cyclopropyl | 1H NMR(CDCl3): δ = 0.91; 1.26; 2.74; 2.96; 7.61 ppm |
| 112 | Cl | H | CF3 | C—Cl | C3H7-i | cyclopropyl | 1H NMR(CDCl3): δ = 1.13; 1.37; 2.86; 3.17; 7.68 ppm |
| 113 | Cl | H | CF3 | C—Cl | —OC4H9-i | cyclopropyl | 1H NMR(CDCl3): δ = 1.04; 2.15; 2.82; 4.07; 7.68 ppm |
| 114 | Cl | H | CF3 | C—Cl | —OCH3 | cyclopropyl | mp.: 128° C. |

TABLE 1-continued

(Ia)

| Ex. No.: | R$^{11}$ | R$^{12}$ | R$^{13}$ | A$^1$ | R$^{14}$ | R$^{15}$ | Physical properties |
|---|---|---|---|---|---|---|---|
| 115 | Cl | H | CF$_3$ | C—Cl | C$_4$H$_9$-i | CH$_3$ | mp.: 93° C. |
| 116 | Cl | H | CF$_3$ | C—Cl | C$_4$H$_9$-t | 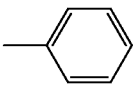 | mp.: 112° C. |
| 117 | Cl | H | CF$_3$ | C—Cl | C$_4$H$_9$-t | CH$_3$ | mp.: 152° C. |
| 118 | Cl | H | CF$_3$ | C—CN | 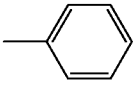 | —NH$_2$ | mp.: 181° C. |
| 119 | Cl | H | CF$_3$ | C—CN |  | 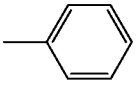 | mp.: 107° C. |
| 120 | Cl | H | CF$_3$ | C—CN | 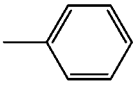 | H | mp.: >250° C. |
| 121 | Cl | H | CF$_3$ | C—CN |  | CH$_3$ | mp.: 158° C. |
| 122 | H$_2$NCS— | H | CF$_3$ | C—Cl | CF$_3$ |  | mp.: 150–152° C. |
| 123 | H$_2$NCO— | H | CF$_3$ | C—Cl | CF$_3$ | 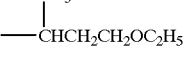 | mp.: 164–166° C. |
| 124 | Cl | H | CF$_3$ | C—Cl | CF$_3$ | —CH(CH$_3$)—C$_6$H$_{11}$ | $^1$H NMR(CDCl$_3$): δ = 1.60–1.65; 4.10–4.20; 7.75 ppm |
| 125 | Cl | H | CF$_3$ | C—Cl | CF$_3$ | —(CH$_2$)$_5$CH$_3$ | $^1$H NMR (CDCl$_3$): δ = 1.80–1.90; 4.85–4.90; 7.75 ppm |
| 126 | Cl | H | CF$_3$ | C—Cl | CF$_3$ | —CH(CH$_3$)CH$_2$CH$_2$OC$_2$H$_5$ | $^1$H NMR(CDCl$_3$): δ = 1.58–1.62; 4.40–4.50; 7.75 ppm |
| 127 | Cl | H | CF$_3$ | C—Cl | CF$_3$ | —CH$_2$CH$_2$OCH$_3$ | $^1$H NMR(CDCl$_3$): δ = 3.40; 3.70–3.75; 7.75 ppm |
| 128 | Cl | H | CF$_3$ | C—CN | CF$_3$ | —CH$_2$CH$_2$OCH$_3$ | mp.: 62–64° C. |
| 129 | Cl | H | CF$_3$ | C—Cl | CF$_3$ |  | mp.: 91–93° C. |
| 130 | Cl | F | CF$_3$ | C—Cl | CF$_2$—CF$_3$ | CH$_3$ | mp.: 129° C. |
| 131 | CF$_3$ | H | CF$_3$ | C—H | CF$_2$—CF$_3$ | CH$_3$ | mp.: 35° C. |
| 132 | CF$_3$ | H | CF$_3$ | C—H | —CHF$_2$ | C$_2$H$_5$ | mp.: 42° C. |
| 133 | Cl | F | CF$_3$ | C—Cl | CF$_3$ | CH$_3$ | mp.: 109° C. |

TABLE 1-continued

(Ia)

| Ex. No.: | $R^{11}$ | $R^{12}$ | $R^{13}$ | $A^1$ | $R^{14}$ | $R^{15}$ | Physical properties |
|---|---|---|---|---|---|---|---|
| 134 | $CF_3$ | H | $CF_3$ | C—H | $CF_3$ | $CH_3$ | mp.: 41° C. |
| 135 | $CF_3$ | H | $CF_3$ | C—H | $CF_3$ |  | mp.: 98° C. |
| 136 | $CF_3$ | H | $CF_3$ | C—H | Br | $CH_3$ | mp.: 110° C. |
| 137 | $CF_3$ | H | $CF_3$ | C—H | $CF_3$ | i-$C_3H_7$ | mp.: 97° C. |
| 138 | Cl | F | $CF_3$ | C—Cl | $CF_3$ | i-$C_3H_7$ | $^1$H NMR(CDCl$_3$): δ = 1.62–164; 4.40; 7.74 ppm |
| 139 | Cl | H | $CF_3$ | C—CN |  |  | mp.: 106° C. |
| 140 | Cl | H | $CF_3$ | C—CN | —$OCH_2$—$CF_3$ |  | mp.: 110° C. |
| 141 | Cl | H | $CF_3$ | C—Cl | —$CH_2$—$C_3H_7$-i |  | oil |
| 142 | Cl | H | $CF_3$ | C—Cl | —O(CH$_2$)$_2$—C(CH$_3$)=CH$_2$ |  | mp.: 81° C. |
| 143 | Cl | H | $CF_3$ | C—Cl |  | —$CH_2$—CH=$CH_2$ | mp.: 82° C. |
| 144 | Cl | H | $CF_3$ | C—Cl | $C_2H_5$ | —$OC_2H_5$ | oil |
| 145 | Cl | H | —$SO_2CF_3$ | C—Cl | —$OCH_2CF_3$ |  | mp.: 113° C. |
| 146 | Cl | H | $CF_3$ | C—Cl | —$OCH_3$ | —$CH_2$—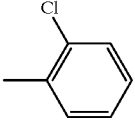 | mp.: 117° C. |
| 147 | Cl | H | $CF_3$ | C—Cl | 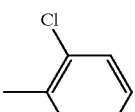 | H | mp.: 215–216° C. |
| 148 | Cl | H | $CF_3$ | C—Cl | 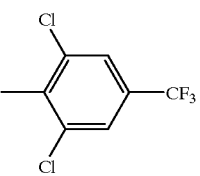 | 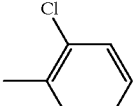 | mp.: 84–86° C. |
| 149 | Cl | H | $CF_3$ | C—Cl | (2-Cl-phenyl) | $CH_3$ | mp.: 115° C. |

TABLE 1-continued

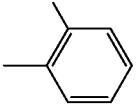

(Ia)

| Ex. No.: | R¹¹ | R¹² | R¹³ | A¹ | R¹⁴ | R¹⁵ | Physical properties |
|---|---|---|---|---|---|---|---|
| 150 | Cl | H | CF₃ | C—CN | 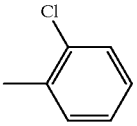 | H | mp.: 198° C. |
| 151 | Cl | H | CF₃ | C—CN | 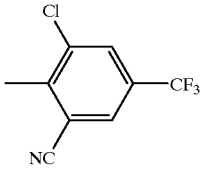 | 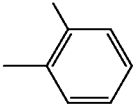 | mp.: 77–79° C. |
| 152 | Cl | H | CF₃ | C—CN | 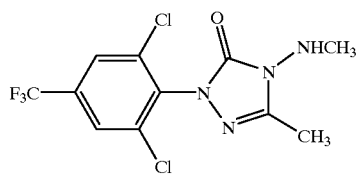 | CH₃ | mp.: 80–82° C. |

USE EXAMPLES

In the following use examples, the compounds listed below are employed as comparison substances:

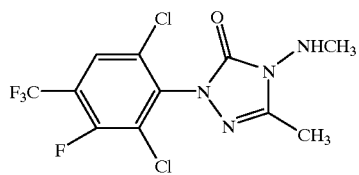

(A)

1-(2,6-dichloro-4-trifluoromethyl-phenyl)-3-methyl-4-methylamino-1,2,4-triazolin-5-one

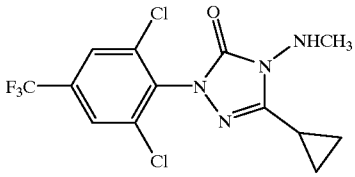

(B)

1-(2,6-dichloro-3-trifluoromethyl-phenyl)-3-methyl-4-methylamino-1,2,4-triazolin-5-one (C)

1-(2,6-dichloro-4-trifluoromethyl-phenyl)-3-cyclopropyl-4-methylamino-1,2,4-triazolin-5-one (All disclosed by EP-A 0 617 026, (A)=Ex. 44, (B)=Ex. 45, (C)=Ex. 72).

Example A

Phaedon Larvae Test
  Solvent: 7 parts by weight of dimethylformamide
  Emulsifier: 1 part by weight of alkylaryl polyglycol ether
  To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with mustard beetle larvae (*Phaedon cochleariae*) while the leaves are still moist.

After the desired period of time, the destruction in % is determined. 100% means that all the beetle larvae have been killed; 0% means that none of the beetle larvae have been killed.

In this test; for example the compounds of Preparation Examples 5, 8, 11, 12, 13, 15, 21, 27, 36, 42, 45, 50, 57 and 83 show a destruction of 100% after 7 days at an exemplary active compound concentration of 0.1%, whereas the known compounds (B) and (C) show no destruction and a destruction of 10%, respectively.

Example B

Plutella Test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the diamond-back moth *Plutella maculipennis* while the leaves are still moist.

After the desired period of time, the destruction in % is determined. 100% means that all the caterpillars have been killed; 0% means that none of the caterpillars have been killed.

In this test, for example the compounds of Preparation Examples 4, 5, 12, 21, 22, 32, 49 and 81 show a destruction of 100% after 7 days at an exemplary active compound concentration of 0.1%, whereas the known compound (C) shows a destruction of 10%.

Example C

*Spodoptera frugiperda* Test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the owlet moth *Spodoptera frugiperda* while the leaves are still moist.

After the desired period of time, the activity in % is determined. 100% means that all the caterpillars have been killed; 0% means that none of the caterpillars have been killed.

In this test, for example the compounds of Preparation Examples 10, 12, 21, 49, and 50 show a destruction of 100% after 7 days at an exemplary active compound concentration of 0.1%, whereas the known compound (C) shows no activity.

Example D

*Heliothis virescens* Test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Soya bean shoots (*Glycine max*) are treated by being dipped into the preparation of active compound of the desired concentration and are infested the the tobacco bud worm *Heliothis virescens* while the leaves are still moist.

After the desired period of time, the destruction in % is determined. 100% means that all the caterpillars have been killed; 0% means that none of the caterpillars have been killed.

In this test, for example the compounds of Preparation Examples 4 and 5 show a destruction of 100% after 7 days at an exemplary active compound concentration of a 0.1%, whereas the known compounds (A) and (B) show no activity.

Example E

Nephotettix Test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Rice seedlings (*Oryza sativa*) are treated by being dipped into the preparation of active compound of the desired concentration and are infested with larvae of the green rice leaf hopper *Nephotettix cincticeps* while the seedlings are still moist.

After the desired period of time, the destruction in % is determined. 100% means that all the leaf hoppers have been killed; 0% means that none of the leaf hoppers have been killed.

In this test; for example the compounds of Preparation Examples 12, 31 41, 45 and 58 show a destruction of 100% after 6 days at an exemplary active compound concentration of 0.1%, whereas the known compounds (A), (B) and (C) show no activity.

Example F

Test with *Boophilus microplus* Resistant/SP-resistant Parkhurst Strain

Test animals: adult females which have sucked themselves full

Solvent: dimethyl sulphoxide 20 mg of active compound are dissolved in 1 ml of dimethyl sulphoxide, and lower concentrations are prepared by dilution with the same solvent.

The test is carried out in 5 replications, 1 $\mu$l of the solution is injected into the abdomen, and the animals are transferred into dishes and kept in an air-conditioned room. The activity is determined via the inhibition of oviposition. 100% means that no tick has deposited eggs.

In this test, an activity of 100% is shown, for example, by the compounds according to the invention of Preparation Examples 5, 21, 32, 33, 34 and 36 at an exemplary active compound concentration of 20 $\mu$g, whereas the known compounds (A), (B) and (C) show no activity.

Example G

Cockroach Test

Test animals: *Periplaneta americana*

Solvent: 35 parts by weight of ethylene glycol monomethyl ether

Emulsifier: 35 parts by weight of nonylphenol polyglycol ether

To produce a suitable formulation, three parts by weight of active compound are mixed with 7 parts by weight of the abovementioned solvent-emulsifier mixture, and the resulting emulsion concentrate is diluted with water to the respective desired concentration.

2 ml of this active compound preparation are pipetted onto filter paper discs (Ø 9.5 cm) situated in Petri dishes of corresponding size. After the filter discs have dried, 5 test animals *P. americana* are transferred and covered.

The activity of the active compound preparation is determined after 3 days. 100% means that all cockroaches have been killed; 0% means that none of the cockroaches have been killed.

In this test, an activity of 100% is shown, for example, by the compounds according to the invention of Preparation Examples 4, 5, 12, 21, 27, 28, 32, 36, 41 and 50 at an exemplary active compound concentration of 1000 ppm, whereas the known compounds (A), (B) and (C) show no activity.

Example H
Test with Flies (*Musca domestica*)

Test animals: adult *Musca domestica,* Reichswald strain (OP, SP, carbamate-resistant)

Solvent: 35 parts by weight of ethylene glycol monomethyl ether

Emulsifier: 35 parts by weight of nonylphenol polyglycol ether

To produce a suitable formulation, 3 parts by weight of active compound are mixed with 7 parts by weight of the abovementioned solvent-emulsifier mixture, and the resulting emulsion concentrate is diluted with water to the respective desired concentration.

2 ml of this active compound preparation are pipetted onto filter paper dishes (Ø 9.5 cm) situated in Petri dishes of corresponding size. After the filter discs have dried, 25 test animals are transferred into the Petri dish and covered.

The activity of the active compound preparation is determined after 1, 3, 5 and 24 hours. 100% means that all the flies have been killed; 0% means that none of the flies have been killed.

In this test, an activity of 100% is shown, for example, by the compounds according to the invention of Preparation Examples 4, 5, 8, 12, 21, 22, 23, 24 28, 32, 33 and 36 at an exemplary active compound concentration of 100 ppm, whereas the known compounds (A), (B) and (C) show no activity.

Example I
Test with Fly Larvae/Development-inhibitory Action

Test animals: All larval stages of *Lucilia cuprina* (OP resistant) [pupae and adults (without contact with the active compound)]

Solvent: 35 parts by weight of ethylene glycol monomethyl ether

Emulsifier: 35 parts by weight of nonylphenol polyglycol ether

To produce a suitable formulation, 3 parts by weight of active compound are mixed with 7 parts of the abovementioned solvent-emulsifier mixture, and the resulting emulsion concentrate is diluted with water to the respective desired concentration.

For each individual concentration, 30 to 50 larvae are introduced into a test tube which contains 1 cm$^3$ of horse meat. 500 µl of the dilution to be tested are pipetted onto this horse meat. The test tubes are placed in plastic beakers whose bottom is covered with sea sand, and kept in an air-conditioned room (26° C.±1.5° C., 70%±10% relative humidity). The activity is examined (lervicidal action) after 24 hours and again after 48 hours. After emergence of the larvae (about 72 h), the test tubes are removed and perforated plastic lids are fitted onto the beakers. After 1.5 times the development time (hatching of the control flies), the hatched flies and the pupae/cocoons are counted.

The activity criterion is the incidence of death in the treated larvae after 48 h (larvicidal effect), or the inhibition of the hatching of adults from pupae or the inhibition of pupa formation. The criterion for the in vitro activity of a substance is the inhibition of the development of the flies, or a development standstill before the adult stage. 100% larvicidal action means that all the larvae have been killed after 48 hours. 100% development-inhibitory action means that no adult flies have hatched.

In this test, an activity of 100% is shown, for example, by the compounds according to the invention of Preparation Examples 4, 5, 8, 12, 21, 33, 42 and 50 at an active compound concentration of 1000 ppm, whereas the known compounds (A), (B) and (C) show no activity.

What is claimed is:

1. A compound of the formula (Ia)

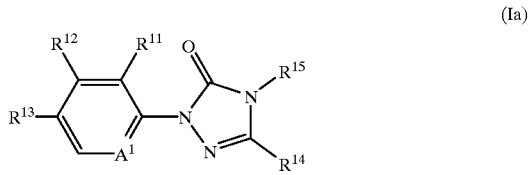

in which

A$^1$ represents the group CR$^o$,

R$^o$ represents hydrogen, fluorine, chlorine, bromine, nitro, cyano, hydroxyl, optionally fluorine-, chlorine-, cyano-, nitro-, or C$_1$–C$_2$-alkoxy-substituted C$_1$–C$_4$-alkyl, optionally fluorine-, chlorine-, bromine-, C$_1$–C$_4$-alkyl-, C$_1$–C$_4$-alkoxy-, C$_1$–C$_4$-halogenoalkyl- or C$_1$–C$_4$-halogenoalkoxy-substituted C$_3$–C$_6$-cycloalkyl, or represents one of the radicals —CONH$_2$, —CSNH$_2$, —CO—NH—C$_1$–C$_4$-alkyl, —CS—NH—C$_1$–C$_4$-alkyl, —CO—N(C$_1$–C$_4$-alkyl)$_2$, or —CS—N(C$_1$–C$_4$-alkyl)$_2$, R$^{11}$ represents fluorine, chlorine, bromine, nitro, cyano, respectively optionally fluorine-, chlorine-, cyano-, nitro- or C$_1$–C$_2$-alkoxy-substituted C$_1$–C$_4$-alkyl or C$_1$–C$_4$-alkoxy, optionally fluorine-, chlorine-, bromine-, C$_1$–C$_4$-alkyl-, C$_1$–C$_4$-alkoxy-, C$_1$–C$_4$-halogenoalkyl- or C$_1$–C$_4$-halogenoalkoxy-substituted C$_3$–C$_6$-cycloalkyl, or represents one of the radicals —CONH$_2$, —CSNH$_2$, —CO—NH—C$_1$–C$_4$-alkyl, —CS—NH—C$_1$–C$_4$-alkyl, —CO—N(C$_1$–C$_4$-alkyl)$_2$ or —CS—N(C$_1$–C$_4$-alkyl)$_2$, R$^{12}$ represents hydrogen, fluorine, chlorine, C$_1$–C$_4$-alkyl or C$_1$–C$_4$-halogenoalkyl, R$^{13}$ represents C$_1$–C$_4$-halogenoalkyl, C$_1$–C$_4$-halogenoalkoxy or one of the radicals —S—C$_1$–C$_4$-halogenoalkyl, —SO—C$_1$–C$_4$-halogenalkyl, or —SO$_2$—C$_1$–C$_4$-halogenoalkyl, R$^{14}$ represents halogen, cyano, respectively optionally fluorine-, chlorine-, cyano-, nitro-, C$_1$–C$_4$-alkoxy- or amino-substituted C$_1$–C$_4$-alkyl or C$_1$–C$_4$-alkoxy, represents C$_3$–C$_6$-alkenyl, C$_3$–C$_6$-alkenyloxy, C$_3$–C$_6$-alkinyl, hydroxyl, mercapto, respectively optionally fluorine-, chlorine-, bromine-, C$_1$–C$_4$-alkyl-, C$_1$–C$_4$-alkoxy-, C$_1$–C$_4$-halogenoalkyl- or C$_1$–C$_4$-halogenoalkoxy-substituted C$_3$–C$_6$-cycloalkyl, or C$_3$–C$_6$-cycloalkyl-C$_1$–C$_4$-alkyl, represents phenyl, phenyloxy-C$_1$–C$_4$-alkyl or phenyl-C$_1$–C$_4$-alkyl, each of which is optionally substituted by halogen, cyano, nitro, C$_1$–C$_4$-alkyl, C$_1$–C$_4$-alkoxy, C$_1$–C$_4$-alkylthio, C$_1$–C$_4$-halogenoalkyl, C$_1$–C$_4$-halogenoalkoxy, C$_1$–C$_4$-halogenoalkylthio or optionally halogen- or C$_1$–C$_4$-alkyl-substituted phenyl, or represents the radical —S(O)$_n$$^1$R$^{16}$, R$^{15}$ represents cyano, amino, respectively optionally fluorine-, chlorine-, cyano-, nitro-, or C$_1$–C$_4$-alkoxy-substituted C$_1$–C$_4$-alkyl or C$_1$–C$_4$-alkoxy, represents amino-substituted C$_1$–C$_4$-alkoxy, represents C$_3$–C$_6$- alkenyl, $C_3$–$C_6$-alkenyloxy, $C_3$–$C_6$-alkinyl, $C_3$–$C_6$-alkinyloxy, respectively optionally fluorine-, chlorine-, bromine-, $C_1$–$C_4$-alkyl, $C_1$–$C_4$-alkoxy-, $C_1$–$C_4$-halogenoalkyl- or $C_1$–$C_4$-halogenoalkoxy-substituted $C_3$–$C_6$-cycloalkyl or $C_3$–$C_6$-cycloalkyl-$C_1$–$C_4$-alkyl, represents phenyl which is optionally substituted by halogen, cyano, nitro, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy, $C_1$–$C_4$-halogenalkylthio or optionally halogen- or $C_1$–$C_4$-alkyl-substituted phenyl, represents optionally $C_1$–$C_4$-alkyl-substituted benzyl or one of the radicals —$S(O)_n^1R^{16}$, or —$N{=}CR^{19}R^{20}$, $R^{16}$ represents optionally fluorine-, chlorine-, cyano- or nitro-substituted $C_1$–$C_4$-alkyl, represents $C_3$–$C_6$-alkenyl, $C_3$–$C_6$-alkanedienyl, $C_3$–$C_6$-alkinyl, optionally fluorine-, chlorine-, bromine-, $C_1$–$C_4$-alkyl, $C_1$–$C_4$-alkoxy-, $C_1$–$C_4$-halogenoalkyl- or $C_1$–$C_4$-halogenoalkoxy-substituted $C_3$–$C_6$-cycloalkyl, or phenyl which is optionally substituted by halogen, cyano, nitro, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy, $C_1$–$C_4$-halogenoalkylthio or optionally halogen- or $C_1$–$C_4$-alkyl-substituted phenyl, $n^1$ represents one of the numbers 0, 1 or 2, $R^{19}$ represents hydrogen, optionally fluorine-, chlorine-, cyano-, nitro-, amino- or $C_1$–$C_4$-alkoxy-substituted $C_1$–$C_4$-alkyl or represents $C_1$–$C_4$-alkoxy and $R^{20}$ represents hydrogen, optionally fluorine-, chlorine-, cyano-, nitro-, amino- or $C_1$–$C_4$-alkoxy-substituted $C_1$–$C_4$-alkyl or represents $C_1$–$C_4$-alkoxy.

2. A compound of the formula (Ia) according to claim 1 in which $A^1$ represents the group $CR^o$, $R^o$ represents hydrogen, fluorine, chlorine, bromine, nitro, cyano, hydroxyl, methyl, ethyl, n- or i-propyl, methoxymethyl, trifluoromethyl, difluoromethyl, chlorodifluoromethyl, dichlorofluoromethyl or represents one of the radicals —$CONH_2$, —$CSNH_2$, —$CONHCH_3$, —$CSNHCH_3$, —$CON(CH_3)_2$, or —$CSN(CH_3)_2$, $R^{11}$ represents fluorine, chlorine, bromine, nitro, cyano, methyl, ethyl, n- or i-propyl, methoxymethyl, trifluoromethyl, difluoromethyl, chlorodifluoromethyl, dichlorofluoromethyl, trifluoromethoxy, difluoromethoxy, trifluoroethoxy or one of the radicals —$CONH_2$, —$CSNH_2$, —$CSNHCH_3$, —$CON(CH_3)_2$, and —$CSN(CH_3)_2$, $R^{12}$ represents hydrogen, fluorine, chlorine, methyl or trifluoromethyl, $R^{13}$ represents trifluoromethyl, difluoromethyl, chlorodifluoromethyl, dichlorofluoromethyl, trifluoromethoxy, difluoromethoxy, chlorodifluoromethoxy, trifluoromethylsulphenyl, trifluoromethyl-sulphinyl or trifluoromethylsulphonyl, $R^{14}$ represents chlorine, bromine, nitro, cyano, methyl, ethyl, n- or i-propyl, n-, i-, s- or t-butyl, methoxy, ethoxy, n- or i-propoxy, n-, i-, s- or t-butoxy, methoxymethyl, methoxyethyl, ethoxymethyl, ethoxyethyl, trifluoromethyl, difluoromethyl, chlorodifluoromethyl, dichlorofluoromethyl, trifluoroethyl, tetrafluoroethyl, pentafluoroethyl, fluoropropyl, trifluoromethoxy, difluoromethoxy, chlorodifluoromethoxy, dichlorofluoromethoxy, trifluoroethoxy, tetrafluoroethoxy, pentafluoroethoxy, cyanomethyl, allyl, allyloxy, propargyl, hydroxyl, mercapto, respectively optionally fluorine-, chlorine-, bromine-, methyl-, ethyl-, methoxy-, trifluoromethyl- or trifluoromethoxy-substituted cyclopropyl, cyclopropylmethyl, cyclopentyl, cyclopentylmethyl, cyclohexyl or cyclohexylmethyl, represents phenyl, phenoxymethyl or benzyl, each of which is optionally substituted by fluorine, chlorine, methyl, methoxy, trifluoromethyl, trifluoromethoxy, methylthio, trifluoromethylthio, nitro, or optionally fluorine-, chlorine- or methyl-substituted phenyl, or represents the radical —$S(O)O_n^1R^{16}$, $R^{15}$ represents cyano, amino, methyl, ethyl, n- or i-propyl, n-, i-, s- or t-butyl, methoxy, ethoxy, n- or i-propoxy, n-, i-, s- or t-butoxy, methoxymethyl, methoxyethyl, ethoxymethyl, ethoxyethyl, difluoromethyl, chlorodifluoromethyl, dichlorofluoromethyl, trifluoroethyl, fluoropropyl, difluoromethoxy, chlorodifluoromethoxy, dichlorofluoromethoxy, cyanomethyl, allyl, allyloxy, propargyl, propargyloxy, butinyloxy, respectively optionally fluorine-, chlorine-, bromine-, methyl-, ethyl-, methoxy-, trifluoromethyl- or trifluoromethoxy-substituted cyclopropyl, cyclopropylmethyl, cyclopentyl, cyclopentylmethyl, cyclohexyl or cyclohexylmethyl, represents phenyl which is optionally substituted by fluorine, chlorine, methyl, methoxy, trifluoromethyl, trifluoromethoxy, methylthio, trifluoromethylthio, cyano, nitro, or optionally fluorine-, chlorine- or methyl-substituted phenyl, represents optionally methyl-, ethyl-, n- or i-propyl-, n-, i-, s- or t-butyl-substituted benzyl or represents one of the radicals —$S(O)_n^1R^{16}$, $NR^{17}R^{18}$, or —$N{=}CR^{19}R^{20}$, $R^{16}$ represents methyl, ethyl, n- or i-propyl, n-, i-, s- or t-butyl, trifluoromethyl, difluoromethyl, chlorodifluoromethyl, dichlorofluoromethyl, trifluoroethyl, tetrafluoroethyl, pentafluoroethyl, fluoropropyl, allyl, allenyl, propargyl, respectively optionally fluorine-, chlorine-, bromine-, methyl-, ethyl-, methoxy-, trifluoromethyl- or trifluoromethoxy-substituted cyclopropyl, cyclopentyl or cyclohexyl, or phenyl which is optionally substituted by fluorine, chlorine, methyl, methoxy, trifluoromethyl, trifluoromethoxy, methylthio, trifluoromethylthio, cyano, nitro, or optionally fluorine-, chlorine- or methyl-substituted phenyl, $n^1$ represents one of the numbers 0, 1 or 2, $R^{19}$ represents hydrogen, methyl, ethyl, n- or i-propyl, n-, i-, s- or t-butyl, methoxy or ethoxy and $R^{20}$ represents hydrogen, methyl, ethyl, n- or i-propyl, n-, i-, s- or t-butyl, methoxy or ethoxy.

* * * * *